(12) United States Patent
Gu et al.

(10) Patent No.: US 6,225,456 B1
(45) Date of Patent: May 1, 2001

(54) RAS SUPPRESSOR SUR-5

(75) Inventors: Trent Gu, Madison, WI (US); Satoshi Orita; Min Han, both of Boulder, CO (US)

(73) Assignee: University Technololy Corporation, Boulder, CO (US)

( * ) Notice: Subject to any disclaimer, the term of this patent is extended or adjusted under 35 U.S.C. 154(b) by 0 days.

(21) Appl. No.: 09/307,265

(22) Filed: May 6, 1999

Related U.S. Application Data

(60) Provisional application No. 60/084,590, filed on May 7, 1998.

(51) Int. Cl.$^7$ .......................... C07H 21/04; C12N 15/63; C12N 15/85; C12N 15/86; C12N 1/20
(52) U.S. Cl. ..................... 536/23.5; 435/320.1; 435/325; 435/252.1
(58) Field of Search .............................. 800/8; 435/2, 6, 435/91.1, 320.1, 325, 252.1; 536/24.3, 24.31, 23.5

(56) References Cited

U.S. PATENT DOCUMENTS

| | | | |
|---|---|---|---|
| 4,650,764 | 3/1987 | Temin et al. | 435/320 |
| 4,683,195 | 7/1987 | Mullis et al. | 435/6 |
| 4,683,202 | 7/1987 | Mullis | 435/91 |
| 4,797,368 | 1/1989 | Carter et al. | 435/320 |
| 4,861,719 | 8/1989 | Miller | 435/236 |
| 4,873,191 | 10/1989 | Wagner et al. | 435/172.3 |
| 4,946,778 | 8/1990 | Ladner et al. | 435/69.6 |
| 4,965,188 | 10/1990 | Mullis et al. | 435/6 |
| 4,980,289 | 12/1990 | Temin et al. | 435/235 |
| 5,068,175 | 11/1991 | Prashad | 435/6 |
| 5,124,263 | 6/1992 | Temin et al. | 435/240.2 |
| 5,139,941 | 8/1992 | Muzyczka et al. | 435/172.3 |
| 5,399,346 | 3/1995 | Anderson et al. | 424/93.21 |
| 5,443,956 | 8/1995 | Carney | 435/7.23 |
| 5,459,127 | 10/1995 | Felgner et al. | 514/7 |

(List continued on next page.)

FOREIGN PATENT DOCUMENTS

| | | |
|---|---|---|
| 178 220 | 1/1992 | (EP) . |
| 185 573 | 5/1992 | (EP) . |
| 488 528 | 11/1995 | (EP) . |
| 453 242 | 8/1996 | (EP) . |
| WO 84/03564 | 9/1984 | (WO) . |
| WO 89/07150 | 8/1989 | (WO) . |
| WO 90/02806 | 3/1990 | (WO) . |
| WO 90/08832 | 8/1990 | (WO) . |
| WO 91/18088 | 11/1991 | (WO) . |

(List continued on next page.)

OTHER PUBLICATIONS

Mullins JJ et al. Hypertension 22:630–633, 1993.*
Cameron ER. Molecular Biotechnology 7:253–265, 1997.*
Hemmer RE et al. Cell 63:1099–1112. 1990.*
Seidel GE. J. Anim. Sci. 71(Suppl. 3):26–33, 1993.*
Hillier et al. GenBank Accession No. R48370, dated May 18, 1995.*
Catalog No. 1230, New England Bioblabs Catalog, 1988–1989.*
Patent Publication RD 37105 A, Mar. 1995/129.
Anderson and Young, Quantitative Filter Hybridization, in *Nucleic Acid Hybridization* [1985].
Beard et al., "Transcription Mapping of Mouse Adenovirus Type I Early Region 3," *Virol.* 175:81–90 [1990].
Beitel et al., "The *Caenorhabditis elegans* gene lin–1 encodes an ETS–domain protein and defines a branch of the vulval induction pathway," *Genes Dev.* 9:3149–3162 [1995].
Bender et al., "Evidence that the Packaging Signal of Moloney Murine Leukemia Virus Extends into the gag Region," *J. Virol.* 61:1639–1646 [1987].
Bernstein et al., "Gene Transfer with Retrovirus Vectors," *Genet. Eng.* 7:235–261 [1985].
Bradley et al., "Formation of Germ–Line Chimaeras From Embryo–Derived Teratocarcinoma Cell Lines," *Nature* 309:255–258 [1984].
Brinster et al., "Factors Affecting the Efficiency of Introducing Foreign DNA into Mice by Microinjecting Eggs," *Proc. Natl. Acad. Sci. USA* 82:4438–4422 [1985].
Chamberlin and Sternberg, "The lin–3/let–23 pathway mediates inductive signalling during male spicule development in *Caenorhabditis elegans,*" *Development* 120:2713–2721 [1994].
Chamberlin et al., "New RNA Polymerase from *Escherichia coli* Infected with Bacteriophage T7," *Nature* 228:227–231 [1970].
Church et al., "Three genes of the MAP kinase cascade, mek–2, mpk–1/sur–1 and let–60 ras, are required for meiotic cell cycle progression in *Caenorhabditis elegans,*" *Development* 121:2525–2535 [1995].
Clark et al., "The *Caenorhabditis elegans* Locus lin–15, a Negative Regulator of a Tyrosine Kinase Signaling Pathway, Encodes Two Different Proteins," *Genetics* 137:987–997 [1994].
Cole et al., in *Monoclonal Antibodies and Cancer Therapy*, "The EBV–Hybridoma Technique and its Application to Human Lung Cancer," Alan R. Liss, Inc., pp. 77–96 [1995].

(List continued on next page.)

*Primary Examiner*—Scott D. Priebe
*Assistant Examiner*—Ram R. Shukla
(74) *Attorney, Agent, or Firm*—Medlen & Carroll, LLP

(57) ABSTRACT

The present invention relates to Ras suppressors, in particular the Ras suppressor SUR-5. The present invention provides isolated nucleotide sequence encoding SUR-5, isolated SUR-5 peptides, antibodies that specifically bind SUR-5, methods for the detection of SUR-5, methods for producing SUR-5 transgenic animals, non-human animals expressing SUR-5, and methods for screening compounds for the ability to alter SUR-5 associated signal transduction.

12 Claims, 9 Drawing Sheets

U.S. PATENT DOCUMENTS

| | | | |
|---|---|---|---|
| 5,580,859 | 12/1996 | Felgner et al. ........................ | 514/44 |
| 5,582,995 | 12/1996 | Avruch et al. ........................ | 435/71 |
| 5,589,466 | 12/1996 | Felgner et al. ........................ | 514/44 |
| 5,591,582 | 1/1997 | Bos et al. ............................... | 435/6 |
| 5,645,988 | 7/1997 | Van de Woude et al. ............ | 435/6 |
| 5,721,104 | 2/1998 | Chen et al. ........................... | 435/7.1 |
| 5,739,027 | 4/1998 | Kamb .............................. | 435/240.2 |

FOREIGN PATENT DOCUMENTS

| | | |
|---|---|---|
| WO 92/05263 | 4/1992 | (WO) . |
| WO 93/03367 | 2/1993 | (WO) . |
| WO 93/09239 | 5/1993 | (WO) . |
| WO 94/12649 | 6/1994 | (WO) . |
| WO 94/21807 | 9/1994 | (WO) . |
| WO 94/26914 | 11/1994 | (WO) . |
| WO 94/28152 | 12/1994 | (WO) . |
| WO 94/28938 | 12/1994 | (WO) . |
| WO 95/02697 | 1/1995 | (WO) . |
| WO 95/07358 | 3/1995 | (WO) . |
| WO 95/18863 | 7/1995 | (WO) . |
| WO 95/21931 | 8/1995 | (WO) . |
| WO 96/15244 | 5/1996 | (WO) . |
| WO 96/17823 | 6/1996 | (WO) . |
| WO 96/22378 | 7/1996 | (WO) . |
| WO 96/25508 | 8/1996 | (WO) . |
| WO 97/19194 | 5/1997 | (WO) . |
| WO 97/21820 | 6/1997 | (WO) . |

OTHER PUBLICATIONS

Cote et al., "Generation of Human Monoclonal Antibodies Reactive with Cellular Antigens," *Proc. Natl. Acad. Sci. U.S.A.* 80:2026–2030 [1983].

Curiel et al., "High–Efficiency Gene Transfer Mediated by Adenovirus Coupled to DNA–Polylysine Complexes," *Hum. Gene Ther.* 3:147–154 [1992].

Dickson et al., "Raf functions downstream of Ras1 in the Sevenless signal transduction pathway," *Nature* 360:600–603 [1992].

Erlich (ed.), *PCR Technology*, Stockton Press [1989].

Evans et al., "Establishment in Culture of Pluripotential Cells from Mouse Embryos," *Nature* 292:154–156 [1981].

Felgner and Ringold, "Cationic Liposome–Mediated Transfection," *Science* 337:387–388 [1989].

Felgner et. al., "Lipofection: A Highly Efficient, Lipid–Mediated DNA–Transfection Procedure," *Proc. Natl. Acad. Sci. U.S.A.* 84:7413–7417 [1987].

Ferguson et al., "A gentic pathway for the specification of the vulval cell lineages of *Caenorhabditis elegans*," *Nature* 326:259–267 [1987].

Field et al., "Mutations of the Adenylyl Cyclase Gene That Block RAS Function in *Saccharomyces cerevisiae*," *Science* 247:464–467 [1990].

Gossler et al., "Transgenesis by Means of Blastocyst–Derived Embryonic Stem Cell Lines," *Proc. Acad. Sci. USA* 83:9065–9069 [1986].

Graham and van der Eb, "A New Technique for the Assay of Infectivity of Human Adenovirus 5 DNA," *Virol.* 52:456–467 [1973].

Graham, "Covalently closed circles of human adenovirus DNA are infectious," *EMBO J.*, 3:2917–2922 [1984].

Graham et al., "Characteristics of a Human Cell Line Transformed by DNA from Human Adenovirus Type 5," *J. Gen. Virol.* 36:59 [1977].

Gutch et al., "The *Caenorhabditis elegans* SH2 domain–containing protein tyrosine phosphatase PTP–2 participates in signal transduction during oogenesis and vulval development," *Genes Dev.* 12:571–585 [1998].

Han and Sternberg, "Analysis of dominant–negative mutations of the *Caenorhabditis elegans* let–60 ras gene," *Genes Develop.* 5:2188–2198 [1991].

Han et al., "*C. elegans* lin–45 raf gene participates in let–60 ras–stimulated vulval differentiation," *Nature* 363:133–140 [1993].

Harlow and Lane, *Antibodies: A Laboratory Manual*, Cold Spring Harbor Laboratory Press, Cold Spring Harbor, NY.

Haskell and Bowen, "Efficient Production of Transgenic Cattle by Retroviral Infection of Early Embryos," *Mol. Reprod. Dev.* 40:386–390 [1995].

Hogan et al., in *Manipulating the Mouse Embryo*, Cold Spring Harbor Laboratory Press, Cold Spring Harbor, N.Y. [1986].

Huang et al., "The lin–15 Locus Encodes Two Negative Regulators of *Caenorhabditis elegans* Vulval Development," *Mol. Biol. Cell* 5:395–412 [1994].

Huse et al., "Generation of a Large Combinatorial Library of the Immunoglobulin Repertoire in Phage Lambda," *Science* 246:1275–1281 [1989].

Jaenisch, "Transgenic Animals," *Science* 240:1468–1474 [1988].

Jaenisch, "Germ Line Integration and Mendelian Transmission of the Exogenous Moloney Leukemia Virus," *Proc. Natl. Acad. Sci. USA* 73:1260–1264 [1976].

Jahner et al., "De novo methylation and expression of retroviral genomes during mouse embryogenesis," *Nature* 298:623–628 [1982].

Jahner et al., "Insertion of the Bacterial gpt Gene Into the Germ Line of Mice by Retroviral Infection," *Proc. Natl. Acad Sci. USA* 82:6927–6931 [1985].

Kacian et al., "A Replicating RNA Molecule Suitable for a Detailed Analysis of Extracellular Evolution and Replication," *Proc. Natl. Acad. Sci. USA* 69:3038–3042 [1972].

Kaplitt et al., "Expression of a Functional Foreign Gene in Adult Mammalian Brain Following in Vivo Transfer via a Herpes Simplex Virus Type 1 Defective Viral Vector," *Mol. Cell. Neurosci.* 2:320–330 [1991].

Katz and McCormick, "Signal transduction from multiple Ras effectors," *Curr. Opin. Genet. Dev.* 7:75–79 [1997].

Kimble, "Alterations in Cell Lineage following Laser Ablation of Cells in the Somatic Gonad of *Caenorhabditis elegans*," *Dev. Biol.* 87:286–300 [1981].

Kobe et al., "The leucine–rich repeat: a versatile binding motif," *Trends Biochem. Sci.* 19:415–421 [1994].

Köler and Milstein, "Continuous Cultures of Fused Cells Secreting Antibody of Predefined Specificity," *Nature* 256:495–497 [1975].

Kornfeld et al., "The ksr–1 Gene Encodes a Novel Protein Kinase Involved in Ras–Mediated Signaling in C. elegans," *Cell* 83:903–913 [1995].

Kornfeld et al., "The *Caenorhabditis elegans* gene mek–2 is required for vulval induction and encodes a protein similar to the protein kinase MEK," *Genes Dev.* 9:756–768 [1995].

Kornfeld, "Vulval development in *Caenorhabditis elegans*," *Trends Genet.* 13:55–61 [1997].

Kozbor et al., "The Production of Monoclonal Antibodies from Human Lumphocytes," *Immunol. Today* 4:72–79 [1983].

Kuo et al., "Efficient Gene Transfer Into Primary Murine Lymphocytes Obviating the Need for Drug Selection," *Blood* 82:845–852 [1993].

La Salle et al., "An Adenovirus Vector for Gene Transfer into Neurons and Glia in the Brain," *Science* 259:988–990 [1993].

Lebkowski et al., "Adeno–Associated Virus: a Vector System for Efficient Introduction and Integration of DNA into a Variety of Mammalian Cell Types," *Mol. Cell. Biol.* 8:3988–3996 [1988].

Levrero et al., "Defective and nondefective adenovirus vectors for expressing foreign genes in vitro and in vivo," *Gene* 101:195–202 [1991].

Machy, et al., "Gene transfer from targeted liposomes to specific lymphoid cells by electroporation," *Proc. Natl. Acad. Sci. U.S.A.*, 85:8027–8031 [1988].

Mann et al., "Construction of a Retrovirus Packaging Mutant and Its Use to Produce Helper–Free Defective Retrovirus," *Cell* 33:153–159 [1983].

Markowitz et al., "A Safe Packaging Line for Gene Transfer: Separating Viral Genes on Two Different Plasmids," *J. Virol.* 62:1120–1124 [1988].

Marshall, "MAP kinase kinase kinase, MAP kinase kinase and MAP kinase," *Curr. Opin. Genet. Dev.* 4:82–89 [1994].

McCormick, BioTechnol., 3:689 [1985] Reference could not be obtained at this the present time. Applicant will provide copies of the reference upon Examiner's request.

McCormick, "How receptors turn Ras on," *Nature* 363:15–16 [1993].

Mello et al., "Efficient gene transfer in *C. elegans*: extrachromosomal maintenance and integration of transforming sequences," *EMBO J.* 10:3959–3970 [1991].

Miller and Rosman, "Improved Retroviral Vectors for Gene Transfer and Expression," *BioTechniques* 7:980–990 [1992].

Moodie et al., "Complexes of Ras.GTP with Raf–1 and Mitogen–Activated Protein Kinase Kinase," *Science* 260:1658–1661 [1993].

Robertson et al., "Germ–line Transmission of Genes Introduced into cultured Pluipotential Cells by Retroviral Vector," *Nature* 322:445–448 [1986].

Rodriguez–Viciana et al., "Role of Phosphoinositide 3–OH Kinase in Cell Transformation and Control of the Actin Cytoskeleton by Ras," *Cell* 89:457–467 [1997].

Sambrook et al., *Molecular Cloning: A Laboratory Manual*, Cold Spring Harbor Press, NY, pp. 7.39–7.52, 9.31–9.58 [1989].

Samulski et al., "A Recombinant Plasmid from Which an Infectious Adeno–Associated Virus Genome Can Be Excised in Vitro and Its Use to Study Viral Replication," *J. Virol.* 61:3096–3101 [1987].

Samulski et al., "Helper–Free Stocks of Recombinant Adeno–Associated Viruses: Normal Integration Does Not Require Viral Gene Expression," *J. Virol.* 63:3822–3828 [1989].

Smith and Johnson, "Single–step purification of polypeptides expressed in *Escherichia coli* as fusions with glutathione S–transferase," *Gene* 67:31–40 [1988].

Stewart et al., "Expression of Retroviral Vectors in Transgenic Mice Obtained by Embryo Infection," *EMBO J.* 6:383–388 [1987].

Stratford–Perricaudet et al., "Widespread Long–term Gene Transfer to mouse Skeletal Muscles and Heart," *J. Clin. Invest.* 90:626–630 [1992].

Sundaram and Han, "The C. elegans ksr–1 Gene Encodes a Novel Raf–Related Kinase Involved in Ras–Mediated signal Transduction," *Cell* 83:889–901 [1995].

Sundaram et al., "A Ras–mediated signal transduction pathway is involved in the control of sec myoblast migration in *Caenorhabditis elegans*," *Development* 122:2823–2833 [1996].

Suzuki et al., "Leucine–rich repeats and carboxyl terminus are required for interaction of yeast adenylate cyclase with RAS proteins," *Proc. Natl. Acad. Sci.* 87:8711–8715 [1990].

Therrien et al., "KSR, a Novel Protein Kinase Required for RAS Signal Transduction," *Cell* 83:879–888 [1995].

Ulmer et al., "Heterologous Protection Against Influenza by Injection of DNA Encoding a Viral Protein," *Science* 259:1745–1748 [1993].

White et al., "Multiple Ras Functions Can Contribute to Mammalian Cell Transformation," *Cell* 80:533–541 [1995].

Williams et al., "Introduction of Foreign Genes Into Tissues of Living Mice by DNA–coated Microprojectiles," *Proc. Natl. Acad. Sci. U.S.A.* 88:2726–2730 [1991].

Wilson et al., "Hepatocyte–directed Gene Transfer in Vivo Leads to Transient Improvement of Hypercholesterolemia in Low Density Lipoprotein Receptor–deficient Rabbits," *J. Biol. Chem.* 267:963–967 [1992].

Wu and Han, "Suppression of activated Let–60 Ras protein defines a role of *Caenorhabditis elegans* Sur–1 MAP kinase in vulval differentiation," *Genes Dev.* 8:147–159 [1994].

Wu and Wallace, "The Ligation Amplification Reaction (LAR)–Amplification of Specific DNA Sequences Using Sequential Rounds of Template–Dependent Ligation," *Genomics* 4:560–569 [1989].

Wu and Wu, "Receptor–Mediated in Vitro Gene Transformation by a Soluble DNA Carrier System," *J. Biol. Chem.* 262:4429–4432 [1987].

Wu and Wu, "Receptor–Mediated Gene Delivery and Expression in Vivo," *J. Biol. Chem.* 263:14621–14624 [1988].

Yochem et al., "Ras is Required for a Limited Number of Cell Fates and Not for General Proliferation in *Caenorhabditis elegans*," *Mol. Cell Biol.* 17:2716–2722 [1997].

Clark et al., "*C. elegans* cell–signalling gene sem–5 encodes a protein with SH2 and SH3 domains," *Nature* 356:340–344 [1992].

Claudianos & Campbell, "The Novel Flightless–1 Gene Brings Together Two Gene Families, Actin–Binding Proteins Related to Gelsolin and Leucine–Rich–Repeat Proteins Involved in Ras Signal Transduction," *Mol. Biol. Evol.* 12:405–414 [1995].

Cutler and Morrison, "Mammalian Raf–1 is activated by mutations that restore Raf signaling in Drosophila," *The EMBO Journal* 16:1953–1960 [1997].

Han and Sternberg, "let–60, a Gene That Specifies Cell Fates during C. elegans Vulval Induction, Encodes a ras Protein," *Cell* 63:921–931 [1990].

Hara and Han, "Ras farnesyltransferase inhibitors suppress the phenotype resulting from an activated ras mutation in *Caenorhabditis elegans*," *Proc. Natl. Acad. Sci. USA* 92:3333–3337 [1995].

Hughes et al. "Suppression of Integrin Activation: A Novel Function of a Ras/Raf–initiated MAP Kinase Pathway," *Cell* 88:521–530 [1997].

Lackner et al., "A MAP kinase homolog, mpk–1, is involved in ras–mediated induction of vulval cell fates in *Caenorhabditis elegans*," *Genes & Development* 8:160–173 [1994].

Masuelli and Cutler, "Increased Expression of the Ras Suppressor Rsu–1 Enhances Erk–2 Activation and Inhibits Jun Kinase Activation," *Molecular and Cellular Biology* 16:5466–5476 [1996].

Pawson, "Conviction by genetics," *Nature* 356:285–286 [1992].

Pelech, "Signalling pathways: Kinase connections on the cellular intranet," *Curr. Biol.* 6:551–554 (1996).

Sieburth et al., "SUR–8, a Conserved Ras–Binding Protein with Leucine–Rich Repeats, Positively Regulates Ras–Mediated Signaling in *C. elegans*," *Cell* 94 119–130 (1998).

Singh and Han, "sur–2, a novel gene, functions late in the let–60 ras–mediated signaling pathway during *Caenorhabditis elegans* vulval induction," *Genes & Development* 9:2251–2265 [1995].

Sundaram and Han, "Control and integration of cell signaling pathways during *C. elegans* vulval development," *BioEssays* 18:473–480 (1996).

Therrien et al., "KSR modulates signal propagation within the MAPK cascade," *Genes & Development* 10:2684–2695 [1996].

Wu et al., "MEK–2, a *Caenorhabditis elegans* MAP kinase kinase, functions in Ras–mediated vulval induction and other developmental events," *Genes & Development* 9:742–755 (1995).

Xing et al., "The protein kinase KSR interacts with 14–3–3 protein and Raf," *Curr. Biol.* 7:294–300 (1997).

Zhang et al., "Kinase Suppressor of Ras Is Ceramide–Activated Protein Kinase," *Cell* 89:63–72 (1997).

Gu et al., "*Caenorhabditis elegans* SUR–5, a Novel but Conserved Protein, Negatively Regulates LET–60 Ras Activity during Vulval Induction," *Mol. and Cell Biol.*, 8:4456–4564 (1988).

Yochem et al, "A New Marker for Mosaic Analysis in *Caenorhabditis elegans* Indicates a Fusion Between hyp6 and hyp7, Two Major Components of the Hypodermis," *Genetics* 149:1323–1334 (1998).

* cited by examiner

A.
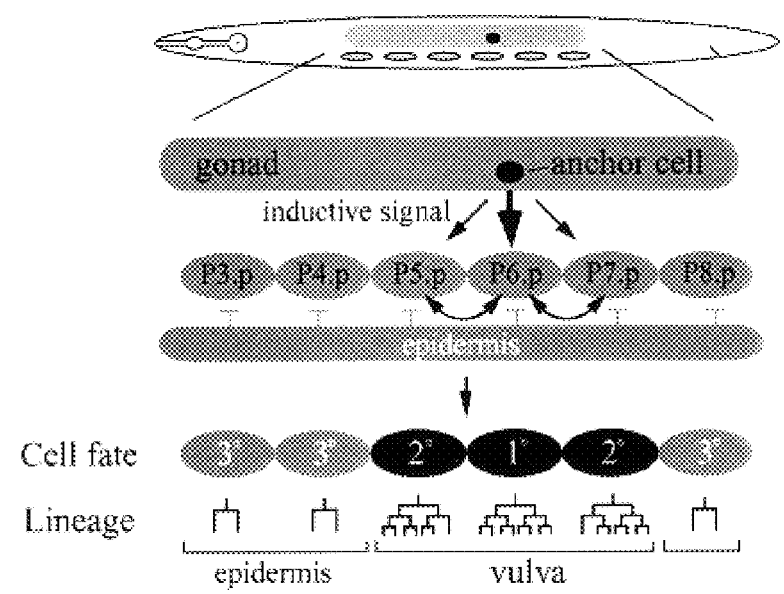
B.
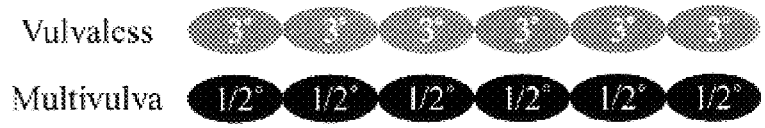
FIG. 1
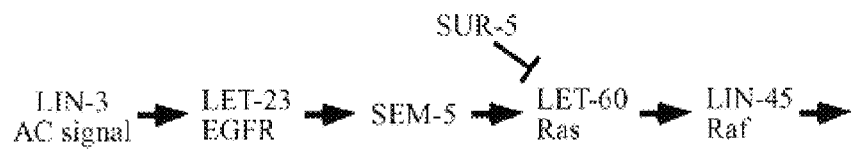
FIG. 2 cDNA Sequence for *C. elegans sur-5* (SEQ ID NO: 1)

```
ATGACCGCAGTGTCTGCAAACGGAAAAACTACCGAAAAGCACGAAAATGGTGCTCACACCAATGGAACGACAAATGGA
ACGACGAATGGATCAATGAATGGAAATGAAATAAGCCATGTTCAGAAACTTCAGCCAGTTTATTACAAGCCGCCACAA
AATTTGGAAACTTTTGAATTGTCACTCAGAAATCATTTTGAAGAGAAAACAAATAAGAAATTTGCTGACTACCGTGAA
TTTCACCGGATTCACTTGTGATAATTATGGTATTTTCTGGGAGGATTTGCTCAAATTGTCCGATGTGAAGCTTCATCAA
AACTACAACCAGGTTATCGATCATAATTTGAAAATCAACGAGAGACCGAGATGGTTCAATGGTGCTACTCTCAACTAT
ACTGAAAATGTCATCGAAAGAGGAACCGCCACCGATATTGCTGTATTGAATGCCAGTATCGAAGAAACAGTGACAGAA
TATACTTACGACAACTTGCGCAAAGATGTTTATCGCATTGCCACATCTCTTCGTAACTATGGAATCGGACCCGGAGAC
ACTGTTTGCGGCTTTGTTCCAAACACATATGACACACTGGTGGCTGTTTTTGCCACAGCCGCTGTCGGAGCTGCCTGG
TGCTCAGCGTCTGTTGATTTTGGACCTGCTGGTGTTCTTGACAGATTCAGACAAGTTCACCCCAAGGTTTTGTTCACA
GTGAATCATGTGACTTACAAGAAGAAGCTCATTGATCAGACCGATAAAATTAATGAAATTGTAAAAGAGCTCCCAACT
CTCGAGAAAATCGTTGTATCCGACACCTTCACATCTGTAAAATTCGATGCAACAAAGTACAATCAAAGTGACAAGTTC
TCATCACTCGAAGAATTCAAGACTCCCATTGCCGATGTTGTGTTGCCATTTGTATATACTCCAGTACCATTTTCCGAT
CCACTCTTCGTAATGTTTAGCTCAGGAACCACGGGAATTCCAAAGGCAATGGTTCACACGGTCGGAGGAACCTTGCTC
AAGCACATTGAGGAGCATTTGGTGCAAGGAGATTCAAAGAAACACGATCGTATGTTTTTCTACACTACATGTGGATGG
ATGATGTATAATTGGATGATCTCGTTCCTATACTCCAAAGGATCTGTTGTATTATTCGATGAATGCCCATTGGCTCCT
GACACCCATATTATCATGAAAATCGCTGCAAAGACACAATCGACTATGATTGGAATGGGTGCGAAGCTTTATGATGAA
TACCTCCGACTTCAAATTCCATTCAACACATTGTACGACCTTTCCAAAATACACACAGTCTACTCGACAGGTTCGCCA
TTGAAGAAAGAGTGCTTCGCTTATATCAACACTTATATTGCGCCAGGCGCTCTCATCGCGTCGATTTCTGGAGGAACT
GACATTATTGGATGCTTTGTCGGTGGTATCAAGTCATTGTCAATCACGCCAGGAGAGTGTCAGTGTTTGTTCCTGGGA
ATGGATATTAAGTCATTCAATTACATGGATGAAGAAATCATTAACTCTGACGAACAAGGAGAGTTAGTGTGTGTCACC
CCATTCCCCTCAATGCCATCACATTTCTTGAATGACACGGATGGCAAGAAGTACCGTGATGCCTACTTTGCTCGCCTA
GAACCATTTTGGGCTCATGGTGATTTTGTGAGAGTGAATCATTCTACGGGCGGTGTAGAAATGCTCGGAAGAAGTGAT
GCTACATTGAATCGCGGCGGAGTTCGAATTGGAACAGCTGAGATTTATTCGGTTGTTGAAAAAATTCCACATATTGCT
GATTGCATTGTAGCTGGAAGACTTGTCGAAGAGGGCATGGACGAGGAAGTTTTGCTGTTTGTGAAAATGGTTCCGGGT
CAAGAGCTCACACACAGTATCCAGGCAGCCATTGTTTCTAAACTCCGGAACGACATGTCCCCGCGACATGTTCCAAAC
AAAATTTACGCAGTTGATGATATTCCGTATACTTCAAGCGGAAAGAAAGTGGAAGTTGCCGTTAAGCAAATTGTGAGT
GGAAAGGCCGTCCAGAAAGCGTCTTCGATTCGCAATCCAGAATCTCTTGATCATTTCGTTCAATACAGACTTTAA
```

FIG. 4 cDNA Sequence for Human *sur-5* (SEQ ID NO: 2)

```
CCCACGCGTCCGATCCTGGAGTGCCAGGTGATGTGGGAGCCTGACAGTAAGAAGAACACGCAGATGGACCGCTTCCGG
GCGGCTGTGGGCGCCGCCTGCGGCCTGGCGCTGGAGAGTTATGATGACTTGTACCATTGGTCCGTTGAGTCATATTCA
GACTTCTGGGCAGAGTTCTGGAAATTCAGTGGAATTGTCTTCTCACGTGTGTATGATGAGGTTGTGGACACATCGAAA
GGAATCGCAGATGTCCCCGAGTGGTTCAAAGGCAGTCGGCTCAACTATGCAGAAAACCTCCTGCGGCACAAAGAGAAT
GACAGAGTTGCCCTTTACATTGCAAGGGAAGGCAAAGAGGAAATTGTGAAGGTGACTTTTGAAGAGCTGAGGCAAGAA
GTGGCTTTGTTTGCAGCAGCAATGAGGAAAATGGGTGTGAAGAAAGGAGATCGGGTTGTTGGTTATTTACCCAACAGT
GAGCACGCTGTCGAGGCGATGCTGGCTGCGGCAAGCATTGGTGCCATCTGGAGCTCCACGTCCCCGGACTTCGGTGTG
AATGGTGTGCTGGACCGGTTTTCTCAAATTCAGCCAAAGCTCATCTTCTCTGTGGAGGCTGTTGTCTATAATGGCAAA
GAGCACAACCACATGGAAAAGCTGCAGCAGGTGGTTAAAGGCCTACCAGACTTGAAGAAAGTGGTGGTGATTCCTTAT
GTGTCCTCCAGAGAGAACATAGACCTTTCAAAGATTCCAAACAGTGTGTTTCTGGATGACTTTCTTGCCACCGGCACC
AGTGAGCAGGCCCCGCAGCTGGAGTTCGAGCAGCTGCCCTTCAGCCACCCACTGTTCATCATGTTCTCATCGGGCACC
ACGGGCGCACCCAAGTGCATGGTGCATTCCGCTGGGGGCACCCTCATCCAGCATCTGAAGGAGCACCTGCTGCACGGC
AACATGACCAGCAGTGACATCCTCCTGTGCTACACCACGGTCGGCTGGATGATGTGGAACTGGATGGTGTCCCTTCTG
GCCACAGGAGCGGCCATGGTCTTGTACGATGGCTCCCCCCTGGTGCCCACGCCCAATGTGCTCTGGGACCTGGTTGAC
AGGATAGGCATCACTGTCCTGGTAACTGGGGCCAAGTGGCTGTCAGTGCTGGAAGAGAAGGCCATGAAGCCGGTGGAA
ACCCACAGTCTCCAGATGCTCCACACGATCCTGTCCACTGGCTCCCCACTGAAAGCCCAGAGCTACGAGTATGTCTAC
AGGTGCATCAAGAGCAGCATCCTCCTGGGCTCCATCTCAGGAGGCACCGACATCATCTCCTGCTTCATGGGCCACAAT
TTTTCTCTTCCTGTGTATAAAGGGGAGATTCAGGCCCGGAACCTGGGCATGGCCGTGGAAGCGTGGAACGAGGAAGGA
AAGGCGGTCTGGGGAGAGAGCGGCGAGCTGGTGTGTACTAAGCCGATCCCTTGCCAGCCCACACACTTCTGGAACGAT
GAGAACGGCAACAAGTACAGGAAGGCGTATTTCTCCAAATTCCCAGGTATCTGGGCTCATGGCGACTACTGCAGAATC
AACCCCAAGACCGGGGGCATCGTCATGCTTGGCCGGAGTGACGGCACCCTCAACCCCAACGGGGTGCGGTTCGGCAGC
TCGGAAATCTATAACATTGTGGAATCCTTCGAGGAGGTGGAGGACAGCCTGTGTGTCCCCCAGTATAACAAGTACAGG
GAGGAGAGGGTGATCCTCTTCCTGAAGATGGCCTCCGGGCACGCCTTCCAGCCTGACTTGGTTAAGAGGATCCGTGAC
GCCATCCGCATGGGCTTGTCTGCGCGACACGTGCCCAGCCTCATCCTGGAAACCAAGGGCATCCCGTATACGCTCAAC
GGCAAGAAAGTGGAAGTTGCCGTCAAACAGATCATCGCTGGAAAAGCCGTGGAGCAAGGAGGTGCTTTCTCGAACCCC
GAGACCCTGGATCTGTACCGGGACATCCCTGAGCTGCAGGGCTTCTGAGTCAGACTGGCTGGCGTGTCACTCAGCCGC
ACCCGTGTGCACTGTAACTTTTGTGTGCTCAAGAAATTATGACAGAAACCTTACAGCTGTTGTGAAAAGGATGGTCGC
ACCAAGTGTTCTGTTAGGCTTTGGGGGAGGGTCCTTTTCTGTGTTTTGTTTAAATGTGGTGGGTACCTGGATCTTTTG
```

FIG. 5

Partial cDNA Sequence for Mouse *sur-5* (SEQ ID NO: 3)

```
CTGGCTGTCAGTGCTGGAGGAGAAGGACATGAAGCCAGTGGAAACTCACAACCTCCACACGCTGCACACGATCCTGTC
CACCGGCTCGCCGCTGAAAGCCCAGAGTTACGAGTATGTGTACAGATGCATCAAGAGCTCCGTGCTCCTGGGCTCCAT
CTCAGGAGGCACTGACATCATCTCCTGTTTCATGGGCCAgAACTCCTCTATTCCTGTGTACAAGGGTGAGATCCAAGC
CCGGAACCTTGGCATGGCTGTGGAAGCCTGGGACgAGGAAGGGAAGGCCGTCTGGGGAGCGAGTGGCgAgCTGGTGTG
CACTAAGCCCATTCCCTGCCAGCCCACGCACTTCTGGAACGACgAGAACGGCAGCAAGTACCGGAAGGCTTACTTCTC
CAAATTCCCAGGTGTCTGGGCACACGGTGACTACTGCAgGGATCAACCCCAAAACAGGAgGCATTATCATGCTGGGCC
GTAGTGATGGCACCCTCAACCCCAATGGCGTCCGCTTTGGCAGCTCGGAGATCTACAACATCGTGGAAGCCTTCGATG
AGGTGGAGGACAGCCTGTGTGTACCCCAGTACAACAGAGATGGCGAGGAGCGGGTGGTCCTGTTCCTGAAGATGGCGT
CCGGGCACACTTTCCAGCCTGACCTCGTGAAGCGCATCCGAGACGCCATCCGACTTGGCCTGTCTGCCCGCCATGTGC
CCAGCCTCATCCTGGAGACCCGAGGCATTCCATACACACTCAATGGCAAGAAAGTGGAGGTGGCCGTGAAGCAGGTGA
TGGCTGGGAGGACTGTGGAGCACCGGGGGGCCTTCTCCAACCCCGAGACCCCCGACTG
```

Predicted Amino Acid Sequence for *C. elegans* SUR-5 (SEQ ID NO: 4)

```
MTAVSANGKTTEKHEMGAHTNGTTNGTTNGSMNGNEISHVQKLQPVYYKPPQNLETFELSLRNHFEEKTNKKFADYRE
FHRFTCDNYGIFWEDLLKLSDVKLHQNYNQVIDHNLKINERPRWFNGATLNYTENVIERGTATDIAVLNASIEETVTE
YTYDNLRKDVYRIATSLRNYGIGPGDTVCGFVPNTYDTLVAVFATAAVGAAWCSASVDFGPAGVLDRFRQVHPKVLFT
VNHVTYKKKLIDQTDKINEIVKELPTLEKIVVSDTFTSVKFDATKYNQSDKFSSLEEFKTPIADVVLPFVYTPVPFSD
PLFVMFSSGTTGIPKAMVHTVGGTLLKHIEEHLVQGDSKKHDRMFFYTTCGWMMYNWMISFLYSKGSVVLFDECPLAP
DTHIIMKIAAKTQSTMIGMGAKLYDEYLRLQIPFNTLYDLSKIHTVYSTGSPLKKECFAYINTYIAPGALIASISGGT
DIIGCFVGGIKSLSITPGECQCLFLGMDIKSFNYMDEEIINSDEQGELVCVTPFPSMPSHFLNDTDGKKYRDAYFARL
EPFWAHGDFVRVNHSTGGVEMLGRSDATLNRGGVRIGTAEIYSVVEKIPHIADCIVAGRLVEEGMDEEVLLFVKMVPG
QELTHSIQAAIVSKLRNDMSPRHVPNKIYAVDDIPYTSSGKKVEVAVKQIVSGKAVQKASSIRNPESLDHFVQYRL
```

FIG. 8

Predicted Amino Acid Sequence for Human SUR-5 (SEQ ID NO: 5)

```
PTRPILECQVMWEPDSKKNTQMDRFRAAVGAACGLALESYDDLYHWSVESYSDFWAEFWKFSGIVFSRVYDEVVDTSK
GIADVPEWFKGSRLNYAENLLRHKENDRVALYIAREGKEEIVKVTFEELRQEVALFAAAMRKMGVKKGDRVVGYLPNS
EHAVEAMLAAASIGAIWSSTSPDFGVNGVLDRFSQIQPKLIFSVEAVVYNGKEHNHMEKLQQVVKGLPDLKKVVVIPY
VSSRENIDLSKIPNSVFLDDFLATGTSEQAPQLEFEQLPFSHPLFIMFSSGTTGAPKCMVHSAGGTLIQHLKEHLLHG
NMTSSDILLCYTTVGWMMWNWMVSLLATGAAMVLYDGSPLVPTPNVLWDLVDRIGITVLVTGAKWLSVLEEKAMKPVE
THSLQMLHTILSTGSPLKAQSYEYVYRCIKSSILLGSISGGTDIISCFMGHNFSLPVYKGEIQARNLGMAVEAWNEEG
KAVWGESGELVCTKPIPCQPTHFWNDENGNKYRKAYFSKFPGIWAHGDYCRINPKTGGIVMLGRSDGTLNPNGVRFGS
SEIYNIVESFEEVEDSLCVPQYNKYREERVILFLKMASGDAFQPDLVKRIRDAIRMGLSARHVPSLILETKGIPYTLN
GKKVEVAVKQIIAGKAVEQGGAFSNPETLDLYRDIPELQGF
```

FIG. 9

Predicted Partial Amino Acid Sequence for Mouse SUR-5 (SEQ ID NO: 6)

```
WLSVLEEKDMKPVETHNLHTLHTILSTGSPLKAQSYEYVYRCIKSSVLLGSISGGTDIISCFMGQNSSIPVYKGEIQA
RNLGMAVEAWDEEGKAVWGASGELVCTKPIPCQPTHFWNDENGSKYRKAYFSKFPGVWAHGDYCRINPKTGGIIMLGR
SDGTLNPNGVRFGSSEIYNIVEAFDEVEDSLCVPQYNRDGEERVVLFLKMASGHTFQPDLVKRIRDAIRLGLSARHVP
SLILETRGIPYTLNGKKVEVAVKQVMAGRTVEHRGAFSNPETPD
```

FIG. 10

SEQUENCE LISTING

<160> NUMBER OF SEQ ID NOS: 16

<210> SEQ ID NO 1
<211> LENGTH: 2103
<212> TYPE: DNA
<213> ORGANISM: Caenorhabditis elegans

<400> SEQUENCE: 1

```
atgaccgcag tgtctgcaaa cggaaaaact accgaaaagc acgaaaatgg tgctcacacc    60
aatggaacga caaatggaac gacgaatgga tcaatgaatg gaaatgaaat aagccatgtt   120
cagaaacttc agccagttta ttacaagccg ccacaaaatt tggaaacttt tgaattgtca   180
ctcagaaatc attttgaaga gaaaacaaat aagaaatttg ctgactaccg tgaatttcac   240
cgattcactt gtgataatta tggtattttc tgggaggatt tgctcaaatt gtccgatgtg   300
aagcttcatc aaaactacaa ccaggttatc gatcataatt tgaaaatcaa cgagagaccg   360
agatggttca atggtgctac tctcaactat actgaaaatg tcatcgaaag aggaaccgcc   420
accgatattg ctgtattgaa tgccagtatc gaagaaacag tgacagaata tacttacgac   480
aacttgcgca aagatgttta tcgcattgcc acatctcttc gtaactatgg aatcggaccc   540
ggagacactg tttgcggctt tgttccaaac acatatgaca cactggtggc tgtttttgcc   600
acagccgctg tcggagctgc ctggtgctca gcgtctgttg attttggacc tgctggtgtt   660
cttgacagat tcagacaagt tcaccccaag gttttgttca cagtgaatca tgtgacttac   720
aagaagaagc tcattgatca gaccgataaa attaatgaaa ttgtaaaaga gctcccaact   780
ctcgagaaaa tcgttgtatc cgacaccttc acatctgtaa aattcgatgc aacaaagtac   840
aatcaaagtg acaagttctc atcactcgaa gaattcaaga ctcccattgc cgatgttgtg   900
ttgccatttg tatatactcc agtaccattt tccgatccac tcttcgtaat gtttagctca   960
ggaaccacgg gaattccaaa ggcaatggtt cacacggtcg gaggaacctt gctcaagcac  1020
attgaggagc atttggtgca aggagattca aagaaacacg atcgtatgtt tttctacact  1080
acatgtggat ggatgatgta taattggatg atctcgttcc tatactccaa aggatctgtt  1140
gtattattcg atgaatgccc attggctcct gacacccata ttatcatgaa aatcgctgca  1200
aagacacaat cgactatgat tggaatgggt gcgaagcttt atgatgaata cctccgactt  1260
caaattccat tcaacacatt gtacgacctt tccaaaatac acacagtcta ctcgacaggt  1320
tcgccattga agaaagagtg cttcgcttat atcaacactt atattgcgcc aggcgctctc  1380
atcgcgtcga tttctggagg aactgacatt attggatgct tgtcggtgg tatcaagtca  1440
```

```
ttgtcaatca cgccaggaga gtgtcagtgt tgttcctgg gaatggatat taagtcattc      1500
aattacatgg atgaagaaat cattaactct gacgaacaag gagagttagt gtgtgtcacc      1560
ccattcccct caatgccatc acatttcttg aatgacacgg atggcaagaa gtaccgtgat      1620
gcctactttg ctcgcctaga accattttgg gctcatggtg attttgtgag agtgaatcat      1680
tctacgggcg gtgtagaaat gctcggaaga agtgatgcta cattgaatcg cggcggagtt      1740
cgaattggaa cagctgagat ttattcggtt gttgaaaaaa ttccacatat tgctgattgc      1800
attgtagctg gaagacttgt cgaagagggc atggacgagg aagttttgct gtttgtgaaa      1860
atggttccgg gtcaagagct cacacacagt atccaggcag ccattgtttc taaactccgg      1920
aacgacatgt ccccgcgaca tgttccaaac aaaatttacg cagttgatga tattccgtat      1980
acttcaagcg gaaagaaagt ggaagttgcc gttaagcaaa ttgtgagtgg aaaggccgtc      2040
cagaaagcgt cttcgattcg caatccagaa tctcttgatc atttcgttca atacagactt      2100
taa                                                                     2103

<210> SEQ ID NO 2
<211> LENGTH: 2184
<212> TYPE: DNA
<213> ORGANISM: Homo sapiens

<400> SEQUENCE: 2
cccacgcgtc cgatcctgga gtgccaggtg atgtgggagc ctgacagtaa gaagaacacg        60
cagatggacc gcttccgggc ggctgtgggc gccgcctgcg gcctggcgct ggagagttat       120
gatgacttgt accattggtc cgttgagtca tattcagact tctgggcaga gttctggaaa       180
ttcagtggaa ttgtcttctc acgtgtgtat gatgaggttg tggacacatc gaaaggaatc       240
gcagatgtcc ccgagtggtt caaaggcagt cggctcaact atgcagaaaa cctcctgcgg       300
cacaaagaga atgacagagt tgcccttta attgcaaggg aaggcaaaga ggaaattgtg       360
aaggtgactt ttgaagagct gaggcaagaa gtggctttgt ttgcagcagc aatgaggaaa       420
atgggtgtga agaaaggaga tcgggttgtt ggttatttac ccaacagtga gcacgctgtc       480
gaggcgatgc tggctgcggc aagcattggt gccatctgga gctccacgtc cccggacttc       540
ggtgtgaatg gtgtgctgga ccggttttct caaattcagc caaagctcat cttctctgtg       600
gaggctgttg tctataatgg caaagagcac aaccacatgg aaaagctgca gcaggtggtt       660
aaaggcctac cagacttgaa gaaagtggtg gtgattcctt atgtgtcctc cagagagaac       720
atagaccttt caaagattcc aaacagtgtg tttctggatg actttcttgc caccggcacc       780
agtgagcagg ccccgcagct ggagttcgag cagctgccct tcagccaccc actgttcatc       840
atgttctcat cgggcaccac gggcgcaccc aagtgcatgg tgcattccgc tgggggcacc       900
ctcatccagc atctgaagga gcacctgctg cacggcaaca tgaccagcag tgacatcctc       960
ctgtgctaca ccacggtcgg ctggatgatg tggaactgga tggtgtccct tctggccaca      1020
ggagcggcca tggtcttgta cgatggctcc ccctggtgc ccacgcccaa tgtgctctgg      1080
gacctggttg acaggatagg catcactgtc ctggtaactg gggccaagtg gctgtcagtg      1140
ctggaagaga aggccatgaa gccggtggaa acccacagtc tccagatgct ccacacgatc      1200
ctgtccactg gctccccact gaaagcccag agctacgagt atgtctacag gtgcatcaag      1260
agcagcatcc tcctgggctc catctcagga ggcaccgaca tcatcctg cttcatgggc      1320 cacaatttt ctcttcctgt gtataaaggg gagattcagg cccggaacct gggcatggcc      1380
```

-continued

```
gtggaagcgt ggaacgagga aggaaaggcg gtctggggag agagcggcga gctggtgtgt    1440
actaagccga tcccttgcca gcccacacac ttctggaacg atgagaacgg caacaagtac    1500
aggaaggcgt atttctccaa attcccaggt atctgggctc atggcgacta ctgcagaatc    1560
aaccccaaga ccgggggcat cgtcatgctt ggccggagtg acggcaccct caaccccaac    1620
ggggtgcggt tcggcagctc ggaaatctat aacattgtgg aatccttcga ggaggtggag    1680
gacagcctgt gtgtccccca gtataacaag tacaggagg agagggtgat cctcttcctg     1740
aagatggcct ccgggcacgc cttccagcct gacttggtta agaggatccg tgacgccatc    1800
cgcatgggct tgtctgcgcg acacgtgccc agcctcatcc tggaaaccaa gggcatcccg    1860
tatacgctca acggcaagaa agtggaagtt gccgtcaaac agatcatcgc tggaaaagcc    1920
gtggagcaag gaggtgcttt ctcgaacccc gagaccctgg atctgtaccg ggacatccct    1980
gagctgcagg gcttctgagt cagactggct ggcgtgtcac tcagccgcac ccgtgtgcac    2040
tgtaactttt gtgtgctcaa gaaattatga cagaaaccct acagctgttg tgaaaaggat    2100
ggtcgcacca agtgttctgt taggctttgg gggagggtcc ttttctgtgt tttgtttaaa    2160
tgtggtgggt acctggatct tttg                                          2184
```

<210> SEQ ID NO 3
<211> LENGTH: 838
<212> TYPE: DNA
<213> ORGANISM: Mus musculus

<400> SEQUENCE: 3

```
ctggctgtca gtgctggagg agaaggacat gaagccagtg gaaactcaca acctccacac      60
gctgcacacg atcctgtcca ccggctcgcc gctgaaagcc cagagttacg agtatgtgta     120
cagatgcatc aagagctccg tgctcctggg ctccatctca ggaggcactg acatcatctc     180
ctgtttcatg ggccagaact cctctattcc tgtgtacaag ggtgagatcc aagcccggaa     240
ccttggcatg gctgtggaag cctgggacga ggaagggaag gccgtctggg agcgagtgg     300 cgagctggtg tgcactaagc ccattccctg ccagcccacg cacttctgga cgacgagaa     360 cggcagcaag taccggaagg cttacttctc caaattccca ggtgtctggg cacacggtga    420
ctactgcagg gatcaacccc aaaacaggag gcattatcat gctgggccgt agtgatggca    480
ccctcaaccc caatggcgtc cgctttggca gctcggagat ctacaacatc gtggaagcct    540
tcgatgaggt ggaggacagc ctgtgtgtac cccagtacaa cagagatggc gaggagcggg    600
tggtcctgtt cctgaagatg gcgtccgggc acactttcca gcctgacctc gtgaagcgca    660
tccgagacgc catccgactt ggcctgtctg ccgccatgt gcccagcctc atcctggaga    720
cccgaggcat tccatacaca ctcaatggca agaaagtgga ggtggccgtg aagcaggtga    780
tggctgggag gactgtggag caccggggg ccttctccaa ccccgagacc cccgactg      838
```

<210> SEQ ID NO 4
<211> LENGTH: 700
<212> TYPE: PRT
<213> ORGANISM: Caenorhabditis elegans

<400> SEQUENCE: 4

Met Thr Ala Val Ser Ala Asn Gly Lys Thr Thr Glu Lys His Glu Asn
 1               5                  10                  15

Gly Ala His Thr Asn Gly Thr Asn Gly Thr Thr Asn Gly Ser Met
            20                  25                  30

-continued

```
Asn Gly Asn Glu Ile Ser His Val Gln Lys Leu Gln Pro Val Tyr Tyr
         35                  40                  45

Lys Pro Pro Gln Asn Leu Glu Thr Phe Glu Leu Ser Leu Arg Asn His
     50                  55                  60

Phe Glu Glu Lys Thr Asn Lys Lys Phe Ala Asp Tyr Arg Glu Phe His
 65                  70                  75                  80

Arg Phe Thr Cys Asp Asn Tyr Gly Ile Phe Trp Glu Asp Leu Leu Lys
                 85                  90                  95

Leu Ser Asp Val Lys Leu His Gln Asn Tyr Asn Gln Val Ile Asp His
             100                 105                 110

Asn Leu Lys Ile Asn Glu Arg Pro Arg Trp Phe Asn Gly Ala Thr Leu
         115                 120                 125

Asn Tyr Thr Glu Asn Val Ile Glu Arg Gly Thr Ala Thr Asp Ile Ala
     130                 135                 140

Val Leu Asn Ala Ser Ile Glu Glu Thr Val Thr Glu Tyr Thr Tyr Asp
145                 150                 155                 160

Asn Leu Arg Lys Asp Val Tyr Arg Ile Ala Thr Ser Leu Arg Asn Tyr
                 165                 170                 175

Gly Ile Gly Pro Gly Asp Thr Val Cys Gly Phe Val Pro Asn Thr Tyr
             180                 185                 190

Asp Thr Leu Val Ala Val Phe Ala Thr Ala Ala Val Gly Ala Ala Trp
         195                 200                 205

Cys Ser Ala Ser Val Asp Phe Gly Pro Ala Gly Val Leu Asp Arg Phe
     210                 215                 220

Arg Gln Val His Pro Lys Val Leu Phe Thr Val Asn His Val Thr Tyr
225                 230                 235                 240

Lys Lys Lys Leu Ile Asp Gln Thr Asp Lys Ile Asn Glu Ile Val Lys
                 245                 250                 255

Glu Leu Pro Thr Leu Glu Lys Ile Val Val Ser Asp Thr Phe Thr Ser
             260                 265                 270

Val Lys Phe Asp Ala Thr Lys Tyr Asn Gln Ser Asp Lys Phe Ser Ser
         275                 280                 285

Leu Glu Glu Phe Lys Thr Pro Ile Ala Asp Val Val Leu Pro Phe Val
     290                 295                 300

Tyr Thr Pro Val Pro Phe Ser Asp Pro Leu Phe Val Met Phe Ser Ser
305                 310                 315                 320

Gly Thr Thr Gly Ile Pro Lys Ala Met Val His Thr Val Gly Gly Thr
                 325                 330                 335

Leu Leu Lys His Ile Glu Glu His Leu Val Gln Gly Asp Ser Lys Lys
             340                 345                 350

His Asp Arg Met Phe Phe Tyr Thr Thr Cys Gly Trp Met Met Tyr Asn
         355                 360                 365

Trp Met Ile Ser Phe Leu Tyr Ser Lys Gly Ser Val Val Leu Phe Asp
     370                 375                 380

Glu Cys Pro Leu Ala Pro Asp Thr His Ile Ile Met Lys Ile Ala Ala
385                 390                 395                 400

Lys Thr Gln Ser Thr Met Ile Gly Met Gly Ala Lys Leu Tyr Asp Glu
                 405                 410                 415

Tyr Leu Arg Leu Gln Ile Pro Phe Asn Thr Leu Tyr Asp Leu Ser Lys
             420                 425                 430

Ile His Thr Val Tyr Ser Thr Gly Ser Pro Leu Lys Lys Glu Cys Phe
         435                 440                 445
```

```
Ala Tyr Ile Asn Thr Tyr Ile Ala Pro Gly Ala Leu Ile Ala Ser Ile
        450                 455                 460

Ser Gly Gly Thr Asp Ile Ile Gly Cys Phe Val Gly Ile Lys Ser
465                 470                 475                 480

Leu Ser Ile Thr Pro Gly Glu Cys Gln Cys Leu Phe Leu Gly Met Asp
                    485                 490                 495

Ile Lys Ser Phe Asn Tyr Met Asp Glu Glu Ile Ile Asn Ser Asp Glu
                500                 505                 510

Gln Gly Glu Leu Val Cys Val Thr Pro Phe Pro Ser Met Pro Ser His
            515                 520                 525

Phe Leu Asn Asp Thr Asp Gly Lys Lys Tyr Arg Asp Ala Tyr Phe Ala
        530                 535                 540

Arg Leu Glu Pro Phe Trp Ala His Gly Asp Phe Val Arg Val Asn His
545                 550                 555                 560

Ser Thr Gly Gly Val Glu Met Leu Gly Arg Ser Asp Ala Thr Leu Asn
                    565                 570                 575

Arg Gly Gly Val Arg Ile Gly Thr Ala Glu Ile Tyr Ser Val Val Glu
                580                 585                 590

Lys Ile Pro His Ile Ala Asp Cys Ile Val Ala Gly Arg Leu Val Glu
            595                 600                 605

Glu Gly Met Asp Glu Val Leu Leu Phe Val Lys Met Val Pro Gly
        610                 615                 620

Gln Glu Leu Thr His Ser Ile Gln Ala Ala Ile Val Ser Lys Leu Arg
625                 630                 635                 640

Asn Asp Met Ser Pro Arg His Val Pro Asn Lys Ile Tyr Ala Val Asp
                    645                 650                 655

Asp Ile Pro Tyr Thr Ser Ser Gly Lys Lys Val Glu Val Ala Val Lys
                660                 665                 670

Gln Ile Val Ser Gly Lys Ala Val Gln Lys Ala Ser Ser Ile Arg Asn
            675                 680                 685

Pro Glu Ser Leu Asp His Phe Val Gln Tyr Arg Leu
    690                 695                 700

<210> SEQ ID NO 5
<211> LENGTH: 665
<212> TYPE: PRT
<213> ORGANISM: Homo sapiens

<400> SEQUENCE: 5

Pro Thr Arg Pro Ile Leu Glu Cys Gln Val Met Trp Glu Pro Asp Ser
  1               5                  10                  15

Lys Lys Asn Thr Gln Met Asp Arg Phe Arg Ala Ala Val Gly Ala Ala
                 20                  25                  30

Cys Gly Leu Ala Leu Glu Ser Tyr Asp Asp Leu Tyr His Trp Ser Val
             35                  40                  45

Glu Ser Tyr Ser Asp Phe Trp Ala Glu Phe Trp Lys Phe Ser Gly Ile
        50                  55                  60

Val Phe Ser Arg Val Tyr Asp Glu Val Asp Thr Ser Lys Gly Ile
65                  70                  75                  80

Ala Asp Val Pro Glu Trp Phe Lys Gly Ser Arg Leu Asn Tyr Ala Glu
                85                  90                  95

Asn Leu Leu Arg His Lys Glu Asn Asp Arg Val Ala Leu Tyr Ile Ala
            100                 105                 110

Arg Glu Gly Lys Glu Glu Ile Val Lys Val Thr Phe Glu Glu Leu Arg
        115                 120                 125
```

```
Gln Glu Val Ala Leu Phe Ala Ala Met Arg Lys Met Gly Val Lys
    130                 135                 140
Lys Gly Asp Arg Val Val Gly Tyr Leu Pro Asn Ser Glu His Ala Val
145                 150                 155                 160
Glu Ala Met Leu Ala Ala Ser Ile Gly Ala Ile Trp Ser Ser Thr
                165                 170                 175
Ser Pro Asp Phe Gly Val Asn Gly Val Leu Asp Arg Phe Ser Gln Ile
                180                 185                 190
Gln Pro Lys Leu Ile Phe Ser Val Glu Ala Val Val Tyr Asn Gly Lys
                195                 200                 205
Glu His Asn His Met Glu Lys Leu Gln Gln Val Lys Gly Leu Pro
    210                 215                 220
Asp Leu Lys Lys Val Val Val Ile Pro Tyr Val Ser Ser Arg Glu Asn
225                 230                 235                 240
Ile Asp Leu Ser Lys Ile Pro Asn Ser Val Phe Leu Asp Asp Phe Leu
                245                 250                 255
Ala Thr Gly Thr Ser Glu Gln Ala Pro Gln Leu Glu Phe Glu Gln Leu
                260                 265                 270
Pro Phe Ser His Pro Leu Phe Ile Met Phe Ser Ser Gly Thr Thr Gly
    275                 280                 285
Ala Pro Lys Cys Met Val His Ser Ala Gly Gly Thr Leu Ile Gln His
    290                 295                 300
Leu Lys Glu His Leu Leu His Gly Asn Met Thr Ser Ser Asp Ile Leu
305                 310                 315                 320
Leu Cys Tyr Thr Thr Val Gly Trp Met Met Trp Asn Trp Met Val Ser
                325                 330                 335
Leu Leu Ala Thr Gly Ala Ala Met Val Leu Tyr Asp Gly Ser Pro Leu
                340                 345                 350
Val Pro Thr Pro Asn Val Leu Trp Asp Leu Val Asp Arg Ile Gly Ile
                355                 360                 365
Thr Val Leu Val Thr Gly Ala Lys Trp Leu Ser Val Leu Glu Glu Lys
    370                 375                 380
Ala Met Lys Pro Val Glu Thr His Ser Leu Gln Met Leu His Thr Ile
385                 390                 395                 400
Leu Ser Thr Gly Ser Pro Leu Lys Ala Gln Ser Tyr Glu Tyr Val Tyr
                405                 410                 415
Arg Cys Ile Lys Ser Ser Ile Leu Leu Gly Ser Ile Ser Gly Gly Thr
                420                 425                 430
Asp Ile Ile Ser Cys Phe Met Gly His Asn Phe Ser Leu Pro Val Tyr
                435                 440                 445
Lys Gly Glu Ile Gln Ala Arg Asn Leu Gly Met Ala Val Glu Ala Trp
    450                 455                 460
Asn Glu Glu Gly Lys Ala Val Trp Gly Glu Ser Gly Glu Leu Val Cys
465                 470                 475                 480
Thr Lys Pro Ile Pro Cys Gln Pro Thr His Phe Trp Asn Asp Glu Asn
                485                 490                 495
Gly Asn Lys Tyr Arg Lys Ala Tyr Phe Ser Lys Phe Pro Gly Ile Trp
                500                 505                 510
Ala His Gly Asp Tyr Cys Arg Ile Asn Pro Lys Thr Gly Gly Ile Val
    515                 520                 525
Met Leu Gly Arg Ser Asp Gly Thr Leu Asn Pro Asn Gly Val Arg Phe
    530                 535                 540
```

-continued

```
Gly Ser Ser Glu Ile Tyr Asn Ile Val Glu Ser Phe Glu Val Glu
545                 550                 555                 560

Asp Ser Leu Cys Val Pro Gln Tyr Asn Lys Tyr Arg Glu Glu Arg Val
            565                 570                 575

Ile Leu Phe Leu Lys Met Ala Ser Gly Asp Ala Phe Gln Pro Asp Leu
                580                 585                 590

Val Lys Arg Ile Arg Asp Ala Ile Arg Met Gly Leu Ser Ala Arg His
            595                 600                 605

Val Pro Ser Leu Ile Leu Glu Thr Lys Gly Ile Pro Tyr Thr Leu Asn
        610                 615                 620

Gly Lys Lys Val Glu Val Ala Val Lys Gln Ile Ile Ala Gly Lys Ala
625                 630                 635                 640

Val Glu Gln Gly Gly Ala Phe Ser Asn Pro Glu Thr Leu Asp Leu Tyr
                    645                 650                 655

Arg Asp Ile Pro Glu Leu Gln Gly Phe
            660                 665
```

<210> SEQ ID NO 6
<211> LENGTH: 278
<212> TYPE: PRT
<213> ORGANISM: Mus musculus

<400> SEQUENCE: 6

```
Trp Leu Ser Val Leu Glu Glu Lys Asp Met Lys Pro Val Glu Thr His
1               5                   10                  15

Asn Leu His Thr Leu His Thr Ile Leu Ser Thr Gly Ser Pro Leu Lys
                20                  25                  30

Ala Gln Ser Tyr Glu Tyr Val Tyr Arg Cys Ile Lys Ser Ser Val Leu
            35                  40                  45

Leu Gly Ser Ile Ser Gly Gly Thr Asp Ile Ile Ser Cys Phe Met Gly
    50                  55                  60

Gln Asn Ser Ser Ile Pro Val Tyr Lys Gly Glu Ile Gln Ala Arg Asn
65                  70                  75                  80

Leu Gly Met Ala Val Glu Ala Trp Asp Glu Gly Lys Ala Val Trp
                85                  90                  95

Gly Ala Ser Gly Glu Leu Val Cys Thr Lys Pro Ile Pro Cys Gln Pro
            100                 105                 110

Thr His Phe Trp Asn Asp Glu Asn Gly Ser Lys Tyr Arg Lys Ala Tyr
        115                 120                 125

Phe Ser Lys Phe Pro Gly Val Trp Ala His Gly Asp Tyr Cys Arg Ile
    130                 135                 140

Asn Pro Lys Thr Gly Gly Ile Ile Met Leu Gly Arg Ser Asp Gly Thr
145                 150                 155                 160

Leu Asn Pro Asn Gly Val Arg Phe Gly Ser Ser Glu Ile Tyr Asn Ile
                165                 170                 175

Val Glu Ala Phe Asp Glu Val Glu Asp Ser Leu Cys Val Pro Gln Tyr
            180                 185                 190

Asn Arg Asp Gly Glu Glu Arg Val Leu Phe Leu Lys Met Ala Ser
        195                 200                 205

Gly His Thr Phe Gln Pro Asp Leu Val Lys Arg Ile Arg Asp Ala Ile
    210                 215                 220

Arg Leu Gly Leu Ser Ala Arg His Val Pro Ser Leu Ile Leu Glu Thr
225                 230                 235                 240

Arg Gly Ile Pro Tyr Thr Leu Asn Gly Lys Lys Val Glu Val Ala Val
                245                 250                 255
```

```
Lys Gln Val Met Ala Gly Arg Thr Val Glu His Arg Gly Ala Phe Ser
            260                 265                 270

Asn Pro Glu Thr Pro Asp
        275
```

<210> SEQ ID NO 7
<211> LENGTH: 26
<212> TYPE: DNA
<213> ORGANISM: Caenorhabditis elegans

<400> SEQUENCE: 7
aactgcagga gggcatggac gaggaa                                      26

<210> SEQ ID NO 8
<211> LENGTH: 30
<212> TYPE: DNA
<213> ORGANISM: Caenorhabditis elegans

<400> SEQUENCE: 8
tcccccgggg aagtctgtat tgaacgaaat                                  30

<210> SEQ ID NO 9
<211> LENGTH: 20
<212> TYPE: DNA
<213> ORGANISM: Caenorhabditis elegans

<400> SEQUENCE: 9
gccaagcttg catgcctgca                                             20

<210> SEQ ID NO 10
<211> LENGTH: 30
<212> TYPE: DNA
<213> ORGANISM: Caenorhabditis elegans

<400> SEQUENCE: 10
gctctagaca ttctgaaaac aaaatctaaa                                  30

<210> SEQ ID NO 11
<211> LENGTH: 8
<212> TYPE: PRT
<213> ORGANISM: Caenorhabditis elegans

<400> SEQUENCE: 11

```
Ala Val Ser Ala Asn Gly Lys Thr
  1               5
```

<210> SEQ ID NO 12
<211> LENGTH: 12
<212> TYPE: PRT
<213> ORGANISM: Caenorhabditis elegans

<400> SEQUENCE: 12

```
Val Met Phe Ser Ser Gly Thr Thr Gly Ile Pro Lys
  1               5                   10
```

<210> SEQ ID NO 13
<211> LENGTH: 12
<212> TYPE: PRT
<213> ORGANISM: Consensus sequence
<220> FEATURE:
<221> NAME/KEY: PEPTIDE
<222> LOCATION: (1)

```
<223> OTHER INFORMATION: The amino acid at this location can be either
      Leucine, Isoleucine, Valine, Methionine, Phenylananine, or
      Tyrosine.
<221> NAME/KEY: PEPTIDE
<222> LOCATION: (2)..(3)
<223> OTHER INFORMATION: The amino acid at this location can be any
      amino acid.
<221> NAME/KEY: PEPTIDE
<222> LOCATION: (4)
<223> OTHER INFORMATION: The amino acid at this location can be either
      Serine, Threonine, or Glycine.
<221> NAME/KEY: PEPTIDE
<222> LOCATION: (5)
<223> OTHER INFORMATION: The amino acid at this location can be either
      Serine, Threonine, Alanine, or Glycine.
<221> NAME/KEY: PEPTIDE
<222> LOCATION: (7)
<223> OTHER INFORMATION: The amino acid at this location can be either
      Serine or Threonine.
<221> NAME/KEY: PEPTIDE
<222> LOCATION: (8)
<223> OTHER INFORMATION: The amino acid at this location can be either
      Serine, Threonine, Glutamic acid, or Isoleucine.
<221> NAME/KEY: PEPTIDE
<222> LOCATION: (9)
<223> OTHER INFORMATION: The amino acid at this location can be either
      Serine or Glycine.
<221> NAME/KEY: PEPTIDE
<222> LOCATION: (10)
<223> OTHER INFORMATION: The amino acid at this location can be any
      amino acid.
<221> NAME/KEY: PEPTIDE
<222> LOCATION: (11)
<223> OTHER INFORMATION: The amino acid at this location can be either
      Proline, Alanine, Serine, Leucine, Isoleucine, Methionine, or U.
<221> NAME/KEY: PEPTIDE
<222> LOCATION: (12)
<223> OTHER INFORMATION: The amino acid at this location can be either
      Lysine or Arginine.

<400> SEQUENCE: 13

Xaa Xaa Xaa Xaa Xaa Gly Xaa Xaa Xaa Xaa Xaa Xaa
 1               5                  10

<210> SEQ ID NO 14
<211> LENGTH: 11
<212> TYPE: PRT
<213> ORGANISM: Caenorhabditis elegans

<400> SEQUENCE: 14

Pro Tyr Thr Ser Ser Gly Lys Lys Val Glu Val
 1               5                  10

<210> SEQ ID NO 15
<211> LENGTH: 11
<212> TYPE: PRT
<213> ORGANISM: Consensus sequence
<220> FEATURE:
<221> NAME/KEY: PEPTIDE
<222> LOCATION: (4)
<223> OTHER INFORMATION: The amino acid at this location can be either
      Arginine, Valine, or Leucine.
<221> NAME/KEY: PEPTIDE
<222> LOCATION: (8)
<223> OTHER INFORMATION: The amino acid at this location can be either
      Isoleucine, Valine, or Threonine.
<221> NAME/KEY: PEPTIDE
<222> LOCATION: (9)
<223> OTHER INFORMATION: The amino acid at this location can be either
      Threonine, Methionine, Valine, or Lysine.
<221> NAME/KEY: PEPTIDE
<222> LOCATION: (11)
```

-continued

```
<223> OTHER INFORMATION: The amino acid at this location can be either
      Arginine or Asparagine.

<400> SEQUENCE: 15

Pro Lys Thr Xaa Ser Gly Lys Xaa Xaa Arg Xaa
 1               5                  10

<210> SEQ ID NO 16
<211> LENGTH: 8
<212> TYPE: PRT
<213> ORGANISM: Consensus sequence
<220> FEATURE:
<221> NAME/KEY: PEPTIDE
<222> LOCATION: (1)
<223> OTHER INFORMATION: The amino acid at this location can be either
      Alanine or Glycine.
<221> NAME/KEY: PEPTIDE
<222> LOCATION: (2)..(5)
<223> OTHER INFORMATION: The amino acid at these locations can be any
      amino acid.
<221> NAME/KEY: PEPTIDE
<222> LOCATION: (8)
<223> OTHER INFORMATION: The amino acid at this location can be either
      Serine or Threonine.

<400> SEQUENCE: 16

Xaa Xaa Xaa Xaa Xaa Gly Lys Xaa
 1               5
```

RAS SUPPRESSOR SUR-5

The present application claims priority to Provisional U.S. Application Serial No. 60/084,590, filed May 7, 1998, now abandoned.

FIELD OF THE INVENTION

The present invention relates to Ras suppressors, in particular the Ras suppressor SUR-5.

BACKGROUND OF THE INVENTION

The Ras family of proteins play critical roles in cell proliferation, differentiation, and cell migration in response to extracellular signals. Ras proteins are small membrane-bound GTPases that act as molecular switches, cycling between an inactive GDP-bound state and an active GTP-bound state. In the most well studied Ras-mediated signal transduction pathways, Ras is activated by receptor tyrosine kinases (RTK) through guanine nucleotide exchange factors that promote GTP binding and a change in Ras conformation to an active state (See e.g., McCormick, Nature 363:15 [1993]). GTP-bound Ras then binds to the serine/threonine kinase Raf and recruits it to plasma membrane where it is activated. Once activated, Raf phosphorylates and activates the dual specific kinase MEK, which in turn phosphorylates and activates MAP kinase. Activated MAP kinase (MAPK) is proposed to regulate the activity of multiple targets including transcription factors for various physiological functions (Marshall, Curr. Opin. Genet. Dev., 4:82 [1994]). Although this model for Ras-dependent signal transduction has been heavily studied, there has been almost no development or identification of effectors that regulate Ras signal transduction or that alter the associated cellular and physiological events stimulated by Ras. Little is known about the nature of Ras effectors or the pathways they control (Rubin et al., WO 97/21820 [1997]).

Recent studies using various model systems including biochemical studies in mammalian tissue culture and genetics in C elegans and Drosophila suggest that the RTK-Ras-MAPK-mediated signal transduction pathway is not a simple linear pathway, but is likely part of complicated signal transduction network (Katz, Curr. Opin. Genet. Dev., 7:15 [1997]; Sundaram and Han, Cell 83, 889 [1995]; and Kornfeld, Trends Genet., 13:55 [1997]). Thus, a series of converging and diverging signalling pathways are likely responsible for the diverse cellular responses mediated by Ras. In recent years, several potential Ras effectors in addition to Raf, including PI3 kinase and Ral GDS, have been described (Katz, supra) and are candidates for defining branch points of Ras signalling. However, these effectors cannot account for all of the cellular responses mediated by Ras (See e.g., White et al., Cell 80:533 [1995]) and have not been sufficiently characterized.

Adding to the complexity of the various signaling processes is the collaboratory roles of multiple factors and signaling branches in regulating the output of the signal. The main players of the RTK-Ras-MAPK pathway may be essential elements of a given signaling process, but there are other factors that feed into or out of this pathway that may play important regulatory functions to ensure maximal activity of the pathway and to tighten the regulation of the signal. For example, the ksr genes were identified as suppressors of activated ras in C. elegans and Drosophila (Sundaram and Han, Cell 83:889 [1995]; Kornfeld et al., Cell 83:903 [1995]; and Therrien et al., Cell 83:879 [1995]), however, their biochemical relation to the Ras pathway is still not well understood. In C. elegans, it has been shown that mutations in the ksr-1 gene do not obviously disrupt vulval signal transduction mediated by ras (i.e., a pathway controlled by ras in C. elegans). However, the ksr-1 activity becomes essential when the activity in the main pathway is compromised (Sundaram and Han, 1995, supra; and Kornfeld et al., 1995, supra).

The art is in need of additional regulators of the Ras signal transduction pathways. To gain regulatory control of Ras signaling and its physiological consequences (e.g., effects on cancer), new Ras effectors and their genes need to be identified and isolated. Without such developments, the ability to control Ras-mediated proliferation, differentiation, and cell migration will be severely limited.

SUMMARY OF THE INVENTION

The present invention relates to Ras suppressors, in particular the Ras suppressor SUR-5.

In one embodiment, the present invention provides an isolated nucleotide sequence encoding at least a portion of a SUR-5 protein. In some embodiments, the isolated nucleotide sequence encodes a SUR-5 protein selected from the group consisting of human SUR-5, murine SUR-5, and C. elegans SUR-5. In certain embodiments the isolated nucleotide sequence is selected from SEQ ID NO:1 (C. elegans), SEQ ID NO:2 (human) and SEQ ID NO:3 (mouse). In another embodiment, the nucleotide sequence further comprises 5' and 3' flanking regions. In yet another embodiment, the nucleotide sequence further comprises intervening regions. In alternative embodiments, the nucleotide sequence comprises portions or fragments of the sequences described above.

In another embodiment, the present invention provides vectors comprising a nucleotide sequence encoding at least a portion of SUR-5. In yet another embodiment, the present invention provides a host cell transformed with a vector comprising a nucleotide sequence encoding at least a portion of SUR-5. It is intended that the nucleotides, as well as the vector comprise deoxyribonucleotides and/or ribonucleotides. It is not intended that the vector be limited to any particular nucleotide sequences. It is also not intended that the host cell be limited to any particular cell type. The host cell may be contained within a living animal, as well as in culture (i.e., in cell cultures). In certain embodiments, the host cell is selected from bacteria, yeast, amphibian, and mammalian cells.

In one embodiment, the present invention provides an isolated peptide sequence comprising at least a fragment of SUR-5. In some embodiments, the isolated peptide sequence is selected from SEQ ID NO:4 (C elegans), SEQ ID NO:5 (human), and SEQ ID NO:6 (mouse), and fragments thereof. The present invention is not limited to proteins and fragments with identical sequences to those disclosed. Indeed, a variety of proteins with altered functions are contemplated including fusion proteins, variants with altered stability and binding specificity, agonists of SUR-5 and antagonists of SUR-5. In a preferred embodiment, a SUR-5-Green Fluorescent Protein fusion protein is provided.

The present invention also provides antibodies capable of specifically binding to any of the polypeptides described above. It is intended that the antibodies be produced using any suitable method known in the art, including polyclonal, as well as monoclonal antibodies. The present invention is not limited to polyclonal or monoclonal antibodies. Indeed, a variety of antigen binding proteins are contemplated, including, but not limited to single chain antibodies, chimeric antibodies, and Fab fragments.

The present invention also provides a polynucleotide sequence comprising at least fifteen nucleotides, capable of hybridizing under stringent conditions to at least a portion of an isolated nucleotide sequence encoding at least a portion of a SUR-5 protein. In certain embodiments, the polynucleotide sequence is selected from the group consisting of SEQ ID NOS:7 and 8.

The present invention also provides methods for detection of a polynucleotide encoding SUR-5 protein in a biological sample suspected of containing the polynucleotide encoding SUR-5, comprising the step of hybridizing at least a portion of the polynucleotide sequence capable of hybridizing under stringent conditions to at least a portion of an isolated nucleotide sequence encoding at least a portion of a SUR-5 protein, to nucleic acid of said biological sample to produce a hybridization complex. In one embodiment, the method further comprises the step of detecting the hybridization complex, wherein the presence of the hybridization complex correlates with the presence of a polynucleotide encoding SUR-5 in the biological sample. In some embodiments, the nucleic acid of the biological sample is amplified.

The present invention also provides a non-human animal overexpressing SUR-5 mRNA in the tissue of the non-human animal. In preferred embodiments, the SUR-5 is human SUR-5. However, SUR-5 mRNA from other species is also encompassed by the present invention. In one embodiment, the non-human animal is a member of the Order Rodentia.

The present invention also provides methods for producing the non-human transgenic animals, comprising the steps of introducing a polynucleotide sequence encoding a SUR-5 protein into an embryonal cell of a non-human animal; transplanting the embryonal target cell formed thereby, into a recipient female parent; and identifying at least one offspring containing the transgene, wherein the SUR-5 mRNA is overexpressed in the tissue of the offspring. In one embodiment, the SUR-5 mRNA is human SUR-5 mRNA. In an alternative embodiment, the SUR-5 protein is a mutant SUR-5 protein.

The present invention also provides a method for screening compounds for the ability to alter SUR-5 signal transduction (i.e., signal transduction pathways where SUR-5 is a component, either directly or indirectly), comprising providing: polypeptide sequence comprising at least a portion of SUR-5, polypeptide sequence comprising at least a portion of a protein known to interact (either directly of indirectly) with SUR-5; and one or more test compounds; combining in any order, the polypeptide sequence comprising at least a portion of SUR-5 and the polypeptide sequence comprising at least a portion of a protein known to interact with SUR-5, and the one or more test compounds; and detecting the presence or absence of an interaction (defined as any detectable interaction, such as covalent binding, physical association, direct or indirect activation or inhibition, etc.) between the polypeptide sequence comprising at least a portion of SUR-5 and the polypeptide sequence comprising at least a portion of a protein known to interact with SUR-5.

DESCRIPTION OF THE FIGURES

FIG. 1 shows a schematic representation of wild type and mutant cell fate specification during C. elegans vulval development.

FIG. 2 shows a schematic of the key genes involved in the main signal transduction pathway of vulval cell fate in C. elegans.

FIG. 4 is the complete cDNA sequence (SEQ ID NO:1) of C. elegans sur-5.

FIG. 5 is the complete cDNA sequence (SEQ ID NO:2) for human sur-5.

FIG. 6 is the partial cDNA sequence (SEQ ID NO:3) for murine sur-5.

FIG. 7 depicts the amino acid sequence alignment of C. elegans SUR-5 (CeSUR-5; SEQ ID NO:4) and its murine (C-terminal partial sequence, MuSUR-5; SEQ ID NO:6) and human homologs (HuSUR-5; SEQ ID NO:5). In this Figure, boxed letters indicate amino acid identity (black) or similarity (gray) between at least two organisms. Gaps are represented by dots. Potential ATP/GTP binding sites are denoted by bars.

FIG. 8 is the predicted amino acid sequence (SEQ ID NO:4) of C. elegans SUR-5.

FIG. 9 is the predicted amino acid sequence (SEQ ID NO:5) of human SUR-5.

FIG. 10 is the predicted partial amino acid sequence (SEQ ID NO:6) of mouse SUR-5.

GENERAL DESCRIPTION OF THE INVENTION

Figure 3:
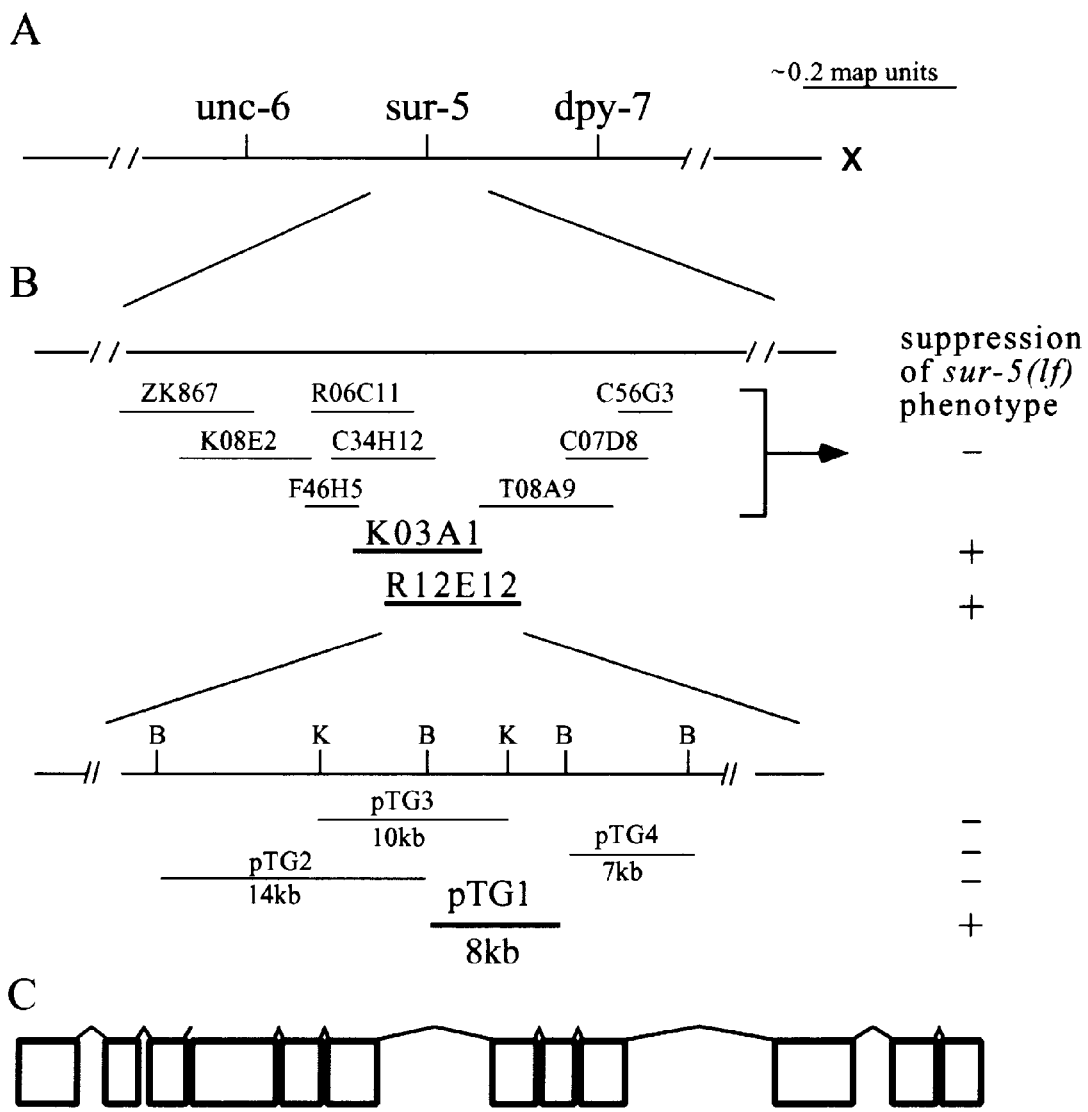
FIG. 3 summarizes the positional cloning of the sur-5 locus. Panel (A) shows the genetic map position of the sur-5 locus; Panel (B) provides an identification of cDNA clones containing the sur-5 gene. In this panel, a partial restriction map within the overlapping region of two positive cosmids is depicted (B, BamHI; K, KpnI); Panel (C) provides the predicted exon (open boxes) and intron (closed boxes) structure of sur-5 gene.

The presently claimed invention relates to Ras suppressors. In particular, the presently claimed invention provides the sur-5 gene (e.g., human sur-5) and methods for identifying, characterizing, and isolating sur-5 genes, SUR-5 proteins, and other Ras effectors. The present invention further provides methods and compositions for targeted therapy directed to sur-5 abnormalities, methods for generating SUR-5 antibodies, and methods for using SUR-5 as a target for screening drugs against Ras. The following provides a description of the identification and cloning of SUR-5. The interactions of sur-5 with other genes and its possible function are also discussed. It is to be noted that the description of sur-5 and its proposed functions contained herein is intended only to describe genetic studies conducted in C. elegans and that the present invention is not limited to a particular mechanism of SUR-5 action. Indeed, an understanding of the mechanism of SUR-5 action is not necessary in order to make and use the present invention.

The C. elegans sur-5 gene was obtained using methods of the present invention. Prior to identification and isolation, C. elegans with dominant negative let-60 (i.e., a gene encoding a C. elegans Ras protein) Ras mutations were constructed to allow for the screening of negative regulators of the Ras-mediated signal transduction pathway. Transgenic animals were treated with mutagen and screening of progeny was conducted for suppressed F2 animals. These suppressor candidates were outcrossed to remove additional mutations from the genome. The animals that retained a suppressive phenotype underwent genetic mapping to assign each of the suppressors to one of the six C. elegans chromosomes. Mapping analysis identified three alleles on X: ku74, ku105, and ku131 (Table 1). sur-5 was mapped to a region between the unc-6 and dpy-7 genes on the X chromosome.

Characterization of the sur-5 gene revealed that it specifically suppresses only one of two groups of let-60 ras dominant negative mutations, and that sur-5 mutations do not have a phenotype of their own. This suggests that the gene may be involved in a specific aspect of Ras activation. Consistent with this negative function, overexpressing sur-5 from an extragenic array partially suppresses the Multivulva phenotype of an activated let-60 ras mutation and causes synergistic phenotypes with a lin-45 raf mutation.

Nucleic acid sequences corresponding to sur-5 were cloned from a cosmid library. Each of two overlapping cosmids, KO3A1 and R12E12, were found to be capable of rescuing the sur-5(ku74) suppression phenotype. A 8 kb BamHI restriction fragment (pTG1) within the overlapping region rescues the suppression phenotype. This fragment was then used to screen a cDNA library to obtain a full-length sur-5 clone (SEQ ID NO:1). A computer structure analysis predicted a 700 amino acid protein (SEQ ID NO:4) encoded by sur-5.

Human (SEQ ID NO:2) and mouse (SEQ ID NO:3) sur-5 genes were identified using homology searches with expressed sequence tag (EST) sequences deposited in the EST Genbank database, isolated, cloned, and characterized. Clones were obtained by probing human and mouse cDNA libraries and using the 5' RACE strategy. Comparison of the predicted amino acid sequences of the human, mouse, and C. elegans sur-5 cDNAs revealed significant homology in the overall structure and sequence between the C. elegans sur-5 and mammalian sur-5.

Additional characterization revealed physical interactions between SUR-5 and Ras. A detailed description of these methods and compositions of the present invention is provided below.

Definitions

To facilitate understanding of the invention, a number of terms are defined below.

As used herein, the term "sur-5" refers to a gene that encodes the "SUR-5" protein.

The term "gene" refers to a nucleic acid (e.g., DNA) sequence that comprises coding sequences necessary for the production of a polypeptide or precursor (e.g., SUR-5). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "sur-5 gene" (or sur-5) refers to the full-length sur-5 nucleotide sequence (e.g., contained in SEQ ID NO:1). However, it is also intended that the term encompass fragments of the sur-5 sequence, as well as other domains within the full-length sur-5 nucleotide sequence. Furthermore, the terms "sur-5 nucleotide sequence" or "sur-5 polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85–100% identity, preferably about 70–100% identity). With medium stringency conditions, nucleic acid base pairing will occur between nucleic acids with an intermediate frequency of complementary base sequences (e.g., hybridization under "medium stringency" conditions may occur between homologs with about 50–70% identity). Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a mammalian SUR-5 protein includes, by way of example, such nucleic acid in cells ordinarily expressing a SUR-5 protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TAA, TAG, TGA).

As used herein, the term "purified" or "to purify" refers to the removal of contaminants from a sample. For example, anti-SUR-5 antibodies are purified by removal of contaminating non-immunoglobulin proteins; they are also purified by the removal of immunoglobulin that does not bind SUR-5. The removal of non-immunoglobulin proteins and/or the removal of immunoglobulins that do not bind SUR-5 results in an increase in the percent of SUR-5-reactive immunoglobulins in the sample. In another example, recombinant SUR-5 polypeptides are expressed in bacterial host cells and the polypeptides are purified by the removal of host cell proteins; the percent of recombinant SUR-5 polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, New York, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39–7.52 [1989]).

The term "Western blot" refers to the analysis of protein (s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign gene that is placed into an organism by introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Embryonal cells at various developmental stages can be used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438–4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873191 describes a method for the micro-injection of zygotes; the disclosure of this patent is incorporated herein in its entirety.

Retroviral infection can also be used to introduce transgenes into a non-human animal. The developing non-human embryo can be cultured in vitro to the blastocyst stage. During this time, the blastomeres can be targets for retroviral infection (Janenich, Proc. Natl. Acad. Sci. USA 73:1260–1264 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (D. Jahner et al., Proc. Natl. Acad Sci. USA 82:6927–693 [1985]). Transfection is easily and efficiently obtained by culturing the blastomeres on a monolayer of virus-producing cells (Van der Putten, supra; Stewart, et al., EMBO J., 6:383–388 [1987]). Alternatively, infection can be performed at a later stage. Virus or virus-producing cells can be injected into the blastocoele (D. Jahner et al., Nature 298:623–628 [1982]). Most of the founders will be mosaic for the transgene since incorporation occurs only in a subset of cells which form the transgenic animal. Further, the founder may contain various retroviral insertions of the transgene at different positions in the genome which generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

A third type of target cell for transgene introduction is the embryonal stem (ES) cell. ES cells are obtained by culturing pre-implantation embryos in vitro under appropriate conditions (Evans et al., Nature 292:154–156 [1981]; Bradley et al., Nature 309:255–258 [1984]; Gossler et al., Proc. Acad. Sci. USA 83:9065–9069 [1986]; and Robertson et al., Nature 322:445–448 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468–1474 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells which have integrated the transgene. This technique obviates the need for growth of the transfected ES cells under appropriate selective conditions prior to transfer into the blastocoel.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis). Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of mRNA present in the band corresponding in size to the correctly spliced SUR-5 transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding sur-5 (e.g., SEQ ID NO:1) or fragments thereof may be employed as hybridization probes. In this case, the sur-5-encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention. In other words, a known therapeutic compound is not limited to a compound efficacious in the regulation of Ras mediated signal transduction pathways.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

DETAILED DESCRIPTION OF THE INVENTION

The ras mediated signal transduction pathway controls cell growth, differentiation, and proliferation in response to extracellular signals. In *C. elegans*, the ras pathway controls vulval cell fate specification in response to a growth factor signal. The *C. elegans* vulva is composed of 22 cells that are all the descendants of three vulval precursor cells (VPCs).

The present invention used C. elegans, a powerful genetic system, and its vulval development to identify and characterize genes that regulate the Ras-mediated signal transduction pathway. In C. elegans, there is a single known ras gene, let-60, that acts in a RTK-Ras-MAPK signal transduction pathway to control several cell fate specification decisions including vulval fate specification. The hermaphrodite vulva is derived from three of six vulval precursor cells (VPCs). Each of the six VPCs has the ability to adopt either a vulval cell fate or a non-vulval cell fate. The proper pattern of cell fate specification is determined by the combination of three signaling events as shown in FIG. 1, illustrating wild type and mutant cell fate specification during vulval development. In this figure, vulval precursor cells P3.p through P8.p form an equivalence group and each cell can take on a vulval cell fate or non vulval cell fate depending on the influence of multiple cell signaling events. An inductive signal from the neighboring anchor cell promotes primary vulval fates by activating a Ras pathway, an inhibitory signal from the surrounding hypodermis promotes tertiary fates and a lateral signal among induced cells promotes secondary fates. In wild type, three of six VPCs adopt a vulval cell fate, and the pattern of cell fate specification is 3° 3° 2° 1° 2° 3° (100% induction). The activated let-60 ras allele, n1046gf or G13E can cause all six VPCs to adopt a vulval cell fate (1°/2°), resulting in a Multivulva phenotype and up to 200% induction. Worms heterozygous for a dominant negative mutation (let-60(K16N dn)) in let-60 exhibit a partial defect in Vulva development (i.e., have a Vulvaless phenotype). Mutations in the sur-5 gene suppress the Vulvaless phenotype caused by this dominant negative mutation.

The signal from the neighboring gonad induces three VPCs to adopt vulval cell fates (Sundaram and Han, BioEssays 18:473 [1996]; and Kornfeld [1997], supra). The key genes involved in the main signal transduction pathway are shown in FIG. 2, along with the proposed sur-5 regulation point. As indicated above, it is not intended that the present invention be limited to a particular mechanism of action. Indeed, an understanding of the mechanism is not necessary to make and use the present invention. Components in this pathway were primarily identified by genetics (Sundaram and Han [1996], supra; and Kornfeld [1997], supra). ksr-1 is a novel kinase that acts to positively regulate the Ras pathway (Sundaram and Han [1995], supra; and Komfeld et al. [1995], supra). sur-5 appears to function to negatively regulate let-60 ras. Mutations that reduce signaling activity cause less than three VPCs to adopt a vulval cell fate (Vulvaless, or Vul). Mutations that cause constitutive activation of the pathway (e.g., activated ras mutations) cause up to all six VPCs to adopt vulval cell fates (Multivulva or Muv). Many genes in the pathway function in multiple cell signaling events during C. elegans development. For example, besides vulval induction, let-60 ras has been shown to function in male tail fate specification (Chamberlin and Stemberg, Develop., 120:2713 [1994]), germ cell and oocyte development (Church et al., Develop., 121, 2525 [1995]); and Gutch et al., Genes Dev., 12, 571 [1998]), sex-myoblast migration (Sundaram et al., Develop., 122:2823 [1996]), and excretory duct cell fate specification (Yochem et al., Mol. Cell Biol., 17:2716 [1997]).

I. Identification and Characterization of C. elegans sur-5

1. Isolation of Suppressors of Dominant Negative let-60 ras

To identify negative regulators in the let-60 ras pathway, a screen was conducted for suppressors of a let-60 dominant negative allele let-60(K16N dn) (genetic allele name sy94; (Han et al., Cell 63:921–931[1990]). Homozygous let-60 (K16N dn) mutations are completely lethal, while heterozygous let-60(K16N dn)/+ worms display a moderately reduced LET-60 protein activity as indicated by the partial defect in vulval development (about 30% VPC induction and 97% egg-laying defective (Egl⁻) (Table 1). This allele was chosen for the screen because (1) it does not poison the let-60 (+) Ras activity completely in the heterozygous mutant; and (2) it has a relatively tight Egl⁻ phenotype (97%) which would facilitate the screening for egg-laying competent (non-Egl⁻) revertants. It is contemplated that this will allow the isolation of a large variety of mutations in different let-60 negative regulators.

Heterozygous worms were mutagenized let-60(K16N)/+ with EMS and then screened for mutations that suppress the Vul phenotype by selecting non-Egl⁻ progeny. Screening of 24,000 mutagenized haploid genomes resulted in the isolation of 13 independent suppressor mutations. Ten suppressors were found to be extragenic, recessive, suppressor mutations. The remaining three suppressors are likely intragenic revertants. The sur-5 gene is defined by three allelic suppressor mutations on X: ku74, ku105, and ku131. sur-5 was mapped to a region between the unc-6 and dpy-7 genes on the X chromosome. It is approximately 0.18 map units to the left of the dpy-7 marker.

TABLE 1

Suppression of ras(dn) by sur-5 Alleles

| sur-5 Genotype[a] | let-60 Genotype[a] | % Egl (n)[b] | % Vulval Differentiation (n)[c] |
|---|---|---|---|
| +/+ | +/+ | 0 | 100 |
| ku74/ku74 | +/+ | 0 (100) | 100 (20) |
| ku105/ku105 | +/+ | 0 (200) | 100 (21) |
| ku131/ku131 | +/+ | 0 (100) | ND[d] |
| +/+ | K16N dn/+ | 97 (300) | 32 (20) |
| ku74/ku74 | K16N dn/+ | 2 (314) | 99 (25) |
| ku105/ku105 | K16N dn/+ | 8 (309) | 83 (20) |
| ku131/ku131 | K16N dn/+ | 3 (398) | ND |
| ku74/uDf1 | K16N dn/+ | ND | 88 (10) |

[a]The complete genotypes for the four groups are (from top to bottom) wild-type N2, sur-5(kuX)/sur-5(kuX), let-60(sy94)/dpy-20(e1326) unc-31 (e169); sur-5(kuX)/sur-5(kuX), and let-60(sy94)/dpy-20(e-126) unc-31 (e169); lon-2(e678) sur-5(ku74)/uDf-1. + indicates wild-type.
[b]Percentage of hermaphrodites that are Egl-. n indicates the number of animals scored.
[c]Percentage of VPCs (P3.p to P8.p) that differentiate into vulval cells relative to the wild-type (100%).
[d]ND, not determined All three sur-5 alleles are similar in their genetic properties. They all revert the let-60(K16N) dominant Egl⁻ phenotype to mostly wild-type. None of them have phenotypes of their own (Table 1), and they all fail to suppress the homozygous lethal phenotype and the mating defect of the let-60(K16N)/+ males. The suppression of the Egl⁻ phenotype is due to increased vulval cell induction as indicated by data from examining two of the sur-5 mutations under Nomarski optics (Table 1). All sur-5 alleles are recessive (data not shown). sur-5(ku74) appears to be the strongest mutation since it suppresses the let-60(K16N dn) Vul phenotype to nearly wild-type. ku74 could be a null allele or a severe loss-of-function allele since a strain of ku74 over a deficiency shows a similar mutant phenotype. However, since the deficiency (uDf1/+) heterozygote itself is not as healthy and has a Egl⁻ phenotype, this test is not conclusive.

As indicated in Table 1, none of the sur-5 alleles can completely revert the let-60(sy94 dn) Vul phenotype. A low percentage of the suppressed animals are still Egl[31]. If these alleles are null or severe loss-of-function mutations, this result may indicate that rather than being a major negative regulator in the Ras pathway such as the lin-1 gene (Beitel et al., Genes Dev., 9:3149–3162 [1995]), sur-5 may have a role in fine tuning the level of let-60 ras activity in the pathway. On the other hand, the sur-5 function could be redundant or partially redundant in *C. elegans*, so that eliminating its function may cause only a small increase in signaling activity.

2. Genetic Interactions Between sur-5 and Mutations in Other Genes in the Signaling Pathway To determine where sur-5 acts in the let-60 Ras pathway, double mutants were constructed between sur-5(ku74) and other loss-of-function mutations of the let-60 ras pathway. The vulval phenotype of these double mutants was then examined. The results are shown in Table 2.

TABLE 2

Genetic Interactions Between sur-5(ku74) and Mutations in Other Genes

| sur-5 Genotype[a] | Other Genotype[a] | % Egl (n)[b] | % VPC Induction (n)[c] |
|---|---|---|---|
| + | let-23(sy1) | 71 (187) | 15 (12) |
| ku74 | let-23(sy1) | 75 (175) | 13 (10) |
| + | sem-5(n2019) | 92 (234) | ND[d] |
| ku74 | sem-5(n2019) | 91 (295) | ND |
| + | let-60(n2021) | 21 (141) | 88 (20) |
| ku74 | let-60(n2021) | 27 (124) | 90 (19) |
| + | lin-45(sy96) | 96 (124) | 30 (12) |
| ku74 | lin-45(sy96) | 97 (140) | 28 (10) |
| + | mpk-1(ku1) | ND[c] | 85 (15) |
| ku74 | mpk-1(ku1) | ND[c] | 81 (11) |
| + | lin-15(n765) | ND[e] | 110 (12)[e] |
| ku74 | lin-15(n765) | ND[e] | 119 (17)[e] |
| + | lin-10(c1439) | 84 (124) | 100 (20) |
| ku74 | lin-10(c1439) | 88 (212) | 100 (22) |
| + | lin-8(n111) | 0 (180) | 100 (20) |
| ku74 | lin-8(n111) | 0 (200) | 100 (22) |
| + | lin-9(n112) | 0 (200) | 100 (22) |
| ku74 | lin-9(n112) | 0 (200) | 100 (48) |

[a]The complete genotypes for the 18 strains are (from top to bottom) let-23 (sy1);lon-2(e678), let-23(sy1); lon-2(e678) sur-5(ku74), lon-2(e678) sem-5 (n2019), lon-2(e678) sur-5(ku74) sem-5(n2019), let-60(n2021); lon-2 (e678), let-60(n2021); lon-2(e678) sur-5(ku-74), unc-24(e138) lin-45 (sy96); lon-2(e678), unc-24(e138) lin-45(sy96); lon-2(e678) sur-5(ku74), dpy-17(e164) mpk-1(ku1), dpy-17(e164) mpk-1(ku1); lon-2(e678) sur-5 (ku74), lon-2(e678) lin-15(n765), lon-2(e678) sur-5(ku74) lin-15(n765), lin-10(e1439); lon-2(e678), lin-10(e1439); lon-2(e678) sur-5(ku74), dpy-10 (e128) lin-8(n111), dpy-10(e128) lin-8(n111); lon-2(e678) sur-5(ku74), dpy-17(e164) lin-9(n112), and dpy-17(e164) lin-9(n112);lon-2(e678) sur-5 (ku74).
[b]Percentage that are egg-laying defective (Egl-). n indicates the number of animals scored.
[c]All lin-15 experiments were done at 17° C.
[d]ND, not determined
[e]The percentages of Egl- animals are not recorded because mpk-1(ku1) has an Egl-phenotype that is not due to lineage defects and lin-15(n765) homozygous worms often have an exploding phenotype that is difficult to distinguish from Egl- phenotypes.

sur-5(ku74) fails to suppress lin-45(sy96) and mpk-1/sur-1(ku1). Since lin-45 and mpk-1 are known positive factors downstream of let-60, this result could suggest that sur-5 does not act downstream of lin-45 and mpk-1. However, sur-5(ku74) also fails to suppress mutations in two genes upstream of let-60 ras, let-23(sy1) and sem-5(n2019). The latter results suggest that the sur-5(ku74) mutation does not cause a significant increase of let-60 ras activity in let-60(+) background which would have suppressed the let-23 alleles (Han et al., Cell 63:921–931[1990]). However, since it is possible that sur-5(ku74) is not a null allele, a null allele might have a stronger effect on mutations in some of the genes tested.

A synthetic Multivulva (syn-Muv) pathway in vulval induction has been previously described (Ferguson et al., Genet., 123:109–121[1989]). Two classes of mutations in this pathway have been recognized, class A and class B. Mutations in either class have no phenotype by themselves, but double mutants containing a mutation in both classes shows a Muv phenotype. Class A and B genes thus define two functionally redundant pathways that negatively regulate vulval induction. To determine if sur-5 belongs to the syn-Muv gene groups, double mutants were constructed between sur-5(ku74) and the class A mutation lin-8(n11) or the class B mutation lin-9(n112). No mutant vulval phenotypes were detected in these strains (Table 2). Therefore, sur-5 is probably not one of the syn-Muv genes.

It is also possible that the sur-5 function is partially redundant to these syn-Muv genes. To test this possibility, a double mutant between sur-5(ku74) and lin-15(n765) was constructed in order to determine whether if sur-5 can enhance the Muv phenotype caused by lin-15. The lin-15 locus contains both class A and class B genes of the syn-Muv gene family. The allele n765 genetically mutates both class A and B genes, and it is temperature-sensitive. The mutant is 100% Muv at 20° C., and about 78% Muv at 15° C. (Ferguson et al., Genet., 110:17–72 [1985]; Hara et al., Proc. Natl. Acad. Aci. USA 92:3333–3337 [1995]). The vulval induction of a sur-5(ku74) lin-15(n765) double mutant at 17° C. was examined using Nomarski optics. It was found that sur-5(ku74) fails to enhance the Muv phenotype of lin-15(n765) at 17° C. (Table 2).

To test if the sur-5 mutations can suppress a loss-of-function ras allele, a sur-5(ku74); let-60(n2021 G75S) double mutant was constructed. let-60(G75S) is a partial loss-of-function mutation that causes 98% lethality. Of the 2% of animals escaping death, some are Vulvaless as adults. It was found that sur-5(ku74) fails to suppress the Vulvaless phenotype of let-60(G75S) escapees (Table 2). It is possible that let-60(G75S) is also mutant in responding to negative regulation by sur-5. This result may suggest that sur-5 is only involved in a specific aspect of regulation of ras activity.

3. Genetic Interactions Between sur-5(ku74) and let-60 dn Mutations

To determine whether suppression by sur-5(ku74) of the dominant Vul phenotype caused by let-60(K16N dn) is allele specific, the ability of sur-5(ku74) to suppress other let-60 dn mutations was tested (Han et al., Genes Dev., 5:2188–2198 [1991]; Han et al., Cell 63:921–931[1990]). sur-5(ku74) is able to suppress four let-60 dn alleles, sy94 (K16N), sy101(G10R), n1531(G15D), and n2301(G15S), but it fails to suppress two other let-60 dn alleles, sy93 (E119N) and sy100(S89F). The results are presented in Table 3. Double mutants between let-60(S89F) and the other two sur-5 alleles were created and it was found that these sur-5 alleles also fail to suppress the dominant Vul phenotype caused by let-60(S89F). All of the let-60(dn) alleles that can be suppressed by sur-5(lf) (called group I alleles) altered the residues within the first conserved loop of the Ras protein that is involved in GTP/GDP binding (Wittinghofer, Cancer Biol., 3:189–198 [1992]). One of the sur-5(lf) non-suppressible alleles (group II alleles) E119N mutates residue 119 on loop 8 that is also involved in nucleotide binding, while the other group II allele S89F mutates residue 89 that might be involved in interacting with other factors. In addition, the group II allele let-60(S89F) is the weakest dominant negative allele based on the percentage of vulval differentiation, while the other group II allele let-60(E93N) is the strongest dominant negative allele (Table 3) (Han et al., Genes Dev., 5:2188–2198 [1991]). Therefore, it is unlikely that the difference in sur-5(lf) suppression between the two groups is due to the strength of the dominant negative effect of the let-60 ras(dn) alleles. The result in Table 3 may suggest that the dominant negative effects of these two groups of ras(dn) mutations are due to two different mechanisms.

TABLE 3

Interaction Between sur-5(ku74) and let-60(dn) Mutations

| Genotype[a] | | | Phenotype | |
|---|---|---|---|---|
| sur-5 | let-60 dn allele | Lesion | % Egl (n) | % Vulval Differentiation (n) |
| +/+ | sy94/+ | K16N | 97 (300) | 32 (20) |
| ku74/ku74 | sy94/+ | K16N | 2 (314) | 99 (25) |
| +/+ | sy101/+ | G10R | 80 (170) | 35 (18) |
| ku74/ku74 | sy101/+ | G10R | 9 (247) | 90 (20) |
| +/+ | n1531/+ | G15D | 88 (228) | 44 (17) |
| ku74/ku74 | n1531/+ | G15D | 4 (418) | 89 (14) |
| +/+ | n2301/+ | G15S | 33 (220) | 81 (16) |
| ku74/ku74 | n2301/+ | G15S | 1 (310) | 99 (21) |
| +/+ | sy93/+ | D119N | 95 (200) | 5 (12) |
| ku74/ku74 | sy93/+ | D119N | 95 (180) | 6 (10) |
| +/+ | sy100/+ | S89F | 25 (418) | 70 (22) |
| ku74/ku74 | sy100/+ | S89F | 25 (257) | 65 (14) |

[a]The complete genotypes for the 12 strains shown are (from top to bottom) let-60(sy94)/dpy-20(e1282) unc-31(e169); let-60(sy94)/dpy-20 (e1362) unc-31(e169); sur-5(ku74), let-60(sy101) dpy-20(e1282)/unc-22 (s9); lon-2(e678), let-60(sy101) dpy-20(e1282)/unc-22(s9); lon-2(e678) sur-5(ku74), let-60(n1531)/dpy-20(e1282); lon-2(e678), let-60(n1531)/dpy-20(e1282); lon-2(e678) sur-5(ku74), let-60(n2301)/dpy-20(e1282); lon-2 (e678), let-60(n2301)/dpy-20(e1282); lon-2(e678) sur-5(ku74), let-60 (sy93)/dpy-20(e1282); lon-2(e678), let-60(sy93)/dpy-20(e1282); lon-2 (e678) sur-5(ku 74), let-60(sy100) dpy-20(e1282)/unc-22(s9); lon-2(e678), and let-60(sy100) dpy-20(e1282)/unc-22(s9); lon-2(e678) sur-5(ku74).
+ indicates wild-type.

4. Phenotypes of Overexpression of sur-5

If sur-5 is a negative regulator of let-60 ras, it is possible that elevating sur-5 activity could suppress the Muv phenotype caused by an activated let-60 ras mutation. Since an extrachromosomal array contains up to hundreds of copies of injected plasmids (Mello et al., EMBO J., 10:3959–3970 [1991]), the effect of over-expressing sur-5 transgenes was tested. The data in Table 4 indicates that an extrachromosomal array carrying a sur-5(+) plasmid partially suppresses the Muv phenotype of let-60(G13E gf) from 89% to 34%. This result is consistent with the hypothesis that sur-5 plays a negative role in the let-60 ras pathway.

TABLE 4

Phenotype of Strains With
Extrachromosomal Arrays Containing sur-5 (+).

| | Phenotype[b] | | | | | |
|---|---|---|---|---|---|---|
| Genotype[a] | % Muv | n | % Egl | % Unc | % Lethality | n |
| let-60(gf);unc-119(lf); Ex unc-119(+) | 89 | 301 | | | | |
| let-60(gf);unc-119(lf); Ex unc-119(+) sur-5 (+) | 34 | 345 | | | | |
| lin-45(ku112) dpy-20(lf) | | | 0 | 0 | 0 | 100 |
| lin-45(ku112) dpy-20(lf); Ex sur-5(5') | | | 0 | 0 | 0 | 124 |
| lin-45(ku112) dpy-20(lf); Ex sur-5 (+) | | | 15 | 64 | 6 | 80 |

[a]The complete genotypes of the five strains are (from top to bottom) let-60 (n1046G13E); unc-119(ed3); Ex pUNC-119(+); let -60(n1046G13E); unc-119(ed3); Ex pUNC119(+) and pTG1_1, lin-45(ku112) dpy-20(e1282), lin-45(ku112) dpy-20(e1282); ExpMH86, pTG96_2 [sur-5(5')-GFP], lin-45 (ku112)dpy-20(e1282); ExpMH86 pTG96_1[sur-5(+)]. pTG96_2[sur-5 (5')] contains GFP fused to the sur-5 promoter and first codon. Ex indicates the chromosomal array.
[b]Muv, animals with a multivulva phenotype observed as multiple ventral protrusions under dissecting microscopes. n is the number of animals scored. Egl, egg-laying defective; Unc, uncoordinated movement.

sur-5 suppression of the Muv phenotype caused by mutations in two other negative regulators lin-15 and lin-1 was tested by introducing an extrachromosomal array carrying the sur-5 transgene (kuEx76) into lin-15(n765) and lin-1 (e1275) mutant animals. No reduction in the percentage of Muv in these transgenic animals was observed. Furthermore, no mutant phenotype was observed when sur-5 was over-expressed from various extrachromosomal arrays in the wild-type background.

Although sur-5 overexpression generates no obvious phenotype in a let-60(+) genetic background, it may still reduce the signaling activity when let-60 ras is wild-type. To observe such a possible effect, the extrachromosomal array kuEx76 was introduced into a strain with a partial loss-of-function mutation of lin-45 raf, ku112. lin-45(ku112) also has no mutant phenotypes in a let-60(+) genetic background but suppresses the Muv phenotype caused by let-60(G13E gf)(Sundaram et al., Cell 83:889–901 [1995]), indicating the Ras-mediated signaling is reduced but not eliminated in the lin-45(ku112) mutant. The sur-5 transgene in the lin-45 (ku112) mutant causes some synergistic mutant phenotypes as shown in Table 4. Sixty four percent of the transgenic animals move very slowly and often show no movement for hours. Such an uncoordinated (Unc) phenotype was unexpected since it was not known that a decrease in let-60 ras pathway activity can lead to an Unc phenotype. This result may suggest that both sur-5 and lin-45raf play a role in cellular functions (e.g., neuronal cell differentiation) that are important for mobility.

Six percent of the transgenic lin-45(ku112); kuEx76 animals died between L1 and L3 developmental stages. Since severe loss-of-function mutations in lin-45 raf have a larval lethal phenotype similar to that in many let-60 ras mutations, the synthetic lethal phenotype caused by overexpression sur-5 in the lin-45(ku112) mutant suggests that sur-5 may also function with let-60 ras during early development.

Fifteen percent of the transgenic animals were found to be egg-laying defective (Egl⁻). However, this synthetic Egl⁻ phenotype appears not to be caused by a reduction in the VPC induction since only wild-type VPC induction was observed in the transgenic animals using Nomarski optics (data not shown). Although it was not possible to determine the cause of this synthetic Egl⁻ phenotype, the phenotype may be consistent with the reduced activity of the signaling pathway. Egl⁻ phenotypes that are not caused by defect in vulval induction are also seen among some other genes functioning in vulval fate specification. For example, certain lin-12 and mpk-1 mutants have a wild-type vulval induction, but are Egl⁻ for reasons that are yet to be determined (Sundaram et al., Genet., 135:755–763 [1993]; Wu et al., Genes. Dev., 8:147–159 [1994]).

Figure 7:
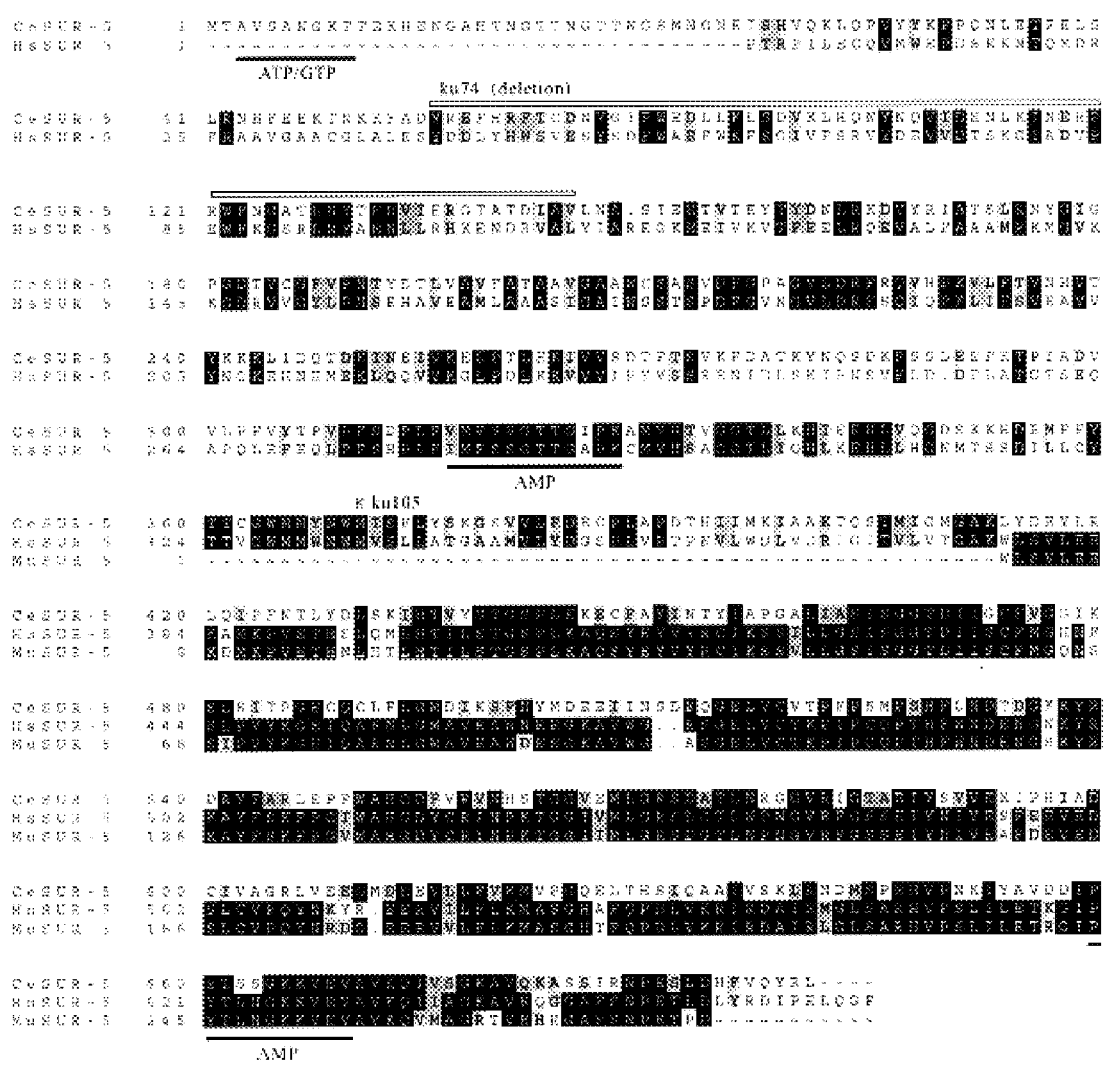

5. The sur-5 Gene Encodes a Novel Gene Product sur-5 was genetically mapped to a small chromosome region between two cloned genes, unc-6 and dpy-7 (0.37 map units) (FIG. 3). sur-5 is estimated to reside between 0.14 and 0.16 map units away from dpy-7 (See, Examples). DNA-mediated microinjection methods were used to identify cosmids that span the region containing the sur-5 gene, using the dominant rol-6 mutant DNA as a marker. The host strain has the genotype let-60(K16N dn)/dpy-20(e1362) unc-31(e169); lon-2(e678) sur-5(ku105). DNA-mediated rescue was assayed by scoring transformants for reversion of the suppressor phenotype of sur-5(ku74) on the let-60 dominant Vul phenotype. The results indicate that each of two overlapping cosmids, K03A1 and R12E12, is capable of rescuing the sur-5(ku74) suppression phenotype (data not shown). After further subcloning and injection, the results indicated that a 8 kb BamHI restriction fragment (pTG1) within the overlapping region of the cosmids K03A1 and R12E12 rescues the sur-5 mutant phenotype. Using this DNA fragment as a probe to screen a cDNA library (gift from P. Okkema and A. Fire), four positive clones were isolated from about 1×10$^6$ plaques. All four cDNA clones have the same sur-5 gene sequence. The sur-5 cDNA sequence is predicted to encode a protein that has 700 amino acids (FIG. 7). Northern analysis using the sur-5 genomic DNA as a probe detected a single transcript approximately 2.2 kb in size which is present in the embryos and larvae.

The computer program PROSITE (distributed by EMBO Laboratory) predicts that SUR-5 has one potential ATP/GTP and two potential AMP binding motifs. Amino acids 3–10, AVSANGKT (SEQ ID NO:12), fit a consensus sequence [AG]-X(4)-G-K-[ST] (SEQ ID NO:16) for an ATP/GTP-binding motif (P-loop; [AG] means the either A or G; X(4) means any 4 amino acids in a row, Saraste et al., Biochem. Sci., 15:430–434 [1990]; Walker et al., EMBO J., 1:945–951 [1982]). Amino acids 315–327, VMFSSGTTGIPK (SEQ ID NO:12), are predicted to be an AMP-binding motif and fit the consensus [LIVMFY]-X(2)-[STG]-[STAG]-G-[ST]-[STEI]-[SG]-X-[PASLIUM]-[KR] (SEQ ID NO:13) (Schroder, Nucl. Acids 17:460–75 [1989]; Smith et al., EMBO J., 9:2743–52 [1990]; Turgay et al., Mol. Microbiol., 6:529–46 [1992]). Another possible AMP-binding motif is at the C-terminus of the SUR-5 amino acid sequence. SUR-5 protein has a relatively weak, but likely significant, sequence similarity to acetyl-CoA synthetases (~21–24% amino acid identity). At the C-terminus of acetyl-CoA synthetases, there is an AMP-binding site consensus (Jung, Mol. Cell. Biol., 14:3707–3718 [1994]). Amino acids 658–669 of SUR-5, PYTSSGKKVEV (SEQ ID NO:14), have similarity to the AMP binding site consensus P-K-T-[RVL]-S-G-K-[IVT]-[TMVK]-R-[RN](SEQ ID NO:15). These sequence features may suggest that SUR-5 protein performs a biochemical function that requires ATP/AMP binding. The similarity to acetyl-CoA synthetases may suggest a function that involves acetyl-CoA.

Molecular lesions of two sur-5 alleles, ku74, and k105 were identified by sequencing the coding region and intron/exon boundaries of the mutant genomic DNA (FIG. 2). It was found that the allele ku74 has a 295 bp in-frame deletion mutation that deletes 70 amino acids (residues 76–145), and creates an extra threonine. Allele ku105 has a point mutation, a T to A change, causing methionine 370 to be replaced by lysine. Methionine 370 is conserved between *C. elegans* sur-5 and its potential mammalian homologs (FIG. 3).

6. Isolation of a Potential Human SUR-5 Homolog.

Using the computer program BLAST, partial DNA sequences of potential mouse and human sur-5 homologs were identified in the EST data base. PCR screening of mouse thymus and human brain cDNA libraries was used to clone additional cDNA sequence 5' to the EST fragments. The total cloned cDNA length (>3.2 kb including >1.2 kb of 3' untranslated region of the EST clones) is similar to the size of a single transcript displayed in a Northern blot, suggesting that the cDNA clone is either full length or approximately full length. The predicted amino acid sequence of the human clone is approximately the size of the *C. elegans* protein. The predicated human protein is about 35% identical to the worm protein and contains all the key features mentioned above (FIG. 7). There is about 90% amino acid identity between the potential human SUR-5 homologs and the partial mouse sequence. This result suggests that the sur-5 gene may be conserved from *C. elegans* to human. Northern analysis also shows that the human gene expressed ubiquitously with higher abundance in brain and testis. A yeast gene that has high degree of similarity in overall structure to the sur-5 gene was not identified.

Similar methods to those discussed above or other methods known in the art can be used to identify sur-5 genes from other species based on the information provided by the present invention. Because of the high degree of sequence similarity in species as diverse as *C. elegans* and humans and between different mammalian species, the sequences provided by the present invention can be used to screen for sur-5 genes in other species where sequence information is available.

7. sur-5 is Strongly Expressed in Most of the Cells in *C. elegans*

To visualize sur-5 expression in vivo, several SUR-5:GFP fusion protein constructs were constructed. One construct, pTG96, includes a 3.68 kb fragment of the 5' flanking sequence and the full length sur-5 genomic sequence fused at its C terminus to the Green Fluorescent Protein (GFP) containing a potent, artificial nuclear localization (NLS) sequence. When transgenic animals carrying pTG96 on an extra-chromosomal array (kuEx75) were examined, the fusion protein, judged by fluorescence of GFP, is observed tightly localized to the nuclei of most cells. SUR-5 appears to be expressed in the VPCs, consistent with a function in regulating Ras activity during vulval induction.

Cell types that express this fusion protein include neurons, hypodermis, Pn.p cells, body muscles, many cells of the pharynx, and a few cells of the somatic gonad. Cells that do not display the fluorescence include B, F, K', K.a, K.p, hyp3, the germline, and the excretory duct cell. In non-mosaic animals, the intensity varies among the cells. The intestine cells and excretory cells are almost always very bright, whereas neurons are almost always fainter. Uterine cells and many of the cells derived from the M cell are very faint and often difficult to see. The SUR-5:GFP fusion proteins are expressed in all stages of *C. elegans* development. The earliest expression is at 100–150 cell embryonic stage, and the fusion proteins are expressed throughout development from that stage on. The same expression pattern is seen when this array is integrated into one of the chromosomes. The intense and broad expression of the sur-5:GFP fusion construct makes it a useful marker for mosaic analysis and for microinjection transformation.

When another SUR-5:GFP construct, pTG96_1 which differs from pTG96 in that it lacks the artificial NLS was expressed, it was found that the extra-chromosomal array (kuEx76) carrying this fusion gene appears to have SUR-5 function, as it can efficiently revert the suppression of let-60(K16N dn) dominant Vul phenotype by sur-5 mutations. This fusion protein is still localized to the nuclei of most cells. The expression pattern is the same as that seen from the array containing pTG96 (with NLS) but the nuclear localization is not as tight. There appears to be some diffusion of SUR-5:GFP proteins from the nucleus to the cytoplasm. Although sur-5 appears to be expressed strongly in the nucleus, it is contemplated that SUR-5 has a function in the cytoplasm since a relatively low amount of SUR-5:GFP fusion protein is detected in cytoplasm.

II. SUR-5 Polynucleotides

The present invention provides nucleic acids corresponding to SUR-5 homologs from the following species: *C. elegans* (SEQ ID NO:1, FIG. 4); human (SEQ ID NO:2, FIG. 5); and mouse (SEQ ID NO:3, FIG. 6). Some embodiments of the present invention provide polynucleotide sequences that are capable of hybridizing to SEQ ID NO:1, SEQ ID NO:2, and SEQ ID NO:3 under conditions of medium to high stringency as long as the polynucleotide sequence capable of hybridizing encodes a protein that retains a biological activity of the naturally occurring SUR-5. In preferred embodiments, hybridization conditions are based on the melting temperature ($T_m$) of the nucleic acid binding complex and confer a defined "stringency" as explained above (See e.g., Wahl, et al., Meth. Enzymol., 152:399–407 [1987], incorporated herein by reference).

In other embodiments of the present invention, alleles of sur-5 are provided. In preferred embodiments, alleles result from a mutation, (i.e., a change in the nucleic acid sequence) and generally produce altered mRNAs or polypeptides whose structure or function may or may not be altered. Any given gene may have none, one or many allelic forms. Common mutational changes which give rise to alleles are generally ascribed to deletions, additions or substitutions of nucleic acids. Each of these types of changes may occur alone, or in combination with the others, and at the rate of one or more times in a given sequence.

In still other embodiments of the present invention, the nucleotide sequences of the present invention may be engineered in order to alter an SUR-5 coding sequence for a variety of reasons, including but not limited to, alterations which modify the cloning, processing and/or expression of the gene product. For example, mutations may be introduced using techniques which are well known in the art (e.g., site-directed mutagenesis to insert new restriction sites, to alter glycosylation patterns, to change codon preference, etc.).

In some embodiments of the present invention, the polynucleotide sequence of SUR-5 may be extended utilizing the nucleotide sequences (e.g., SEQ ID NOS:1, 2, and 3) in various methods known in the art to detect upstream sequences such as promoters and regulatory elements. For example, it is contemplated that restriction-site polymerase chain reaction (PCR) will find use in the present invention. This is a direct method which uses universal primers to retrieve unknown sequence adjacent to a known locus (Gobinda et al., PCR Methods Applic., 2:318–22 [1993]). First, genomic DNA is amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 [1988]). The primers may be designed using Oligo 4.0 (National Biosciences Inc, Plymouth Minn.), or another appropriate program, to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template. In yet another embodiment of the present invention, capture PCR (Lagerstrom et al., PCR Methods Applic., 1:111–19 [1991]) is used. This is a method for PCR amplification of DNA fragments adjacent to a known sequence in human and yeast artificial chromosome (YAC) DNA. Capture PCR also requires multiple restriction enzyme digestions and ligations to place an engineered double-stranded sequence into an unknown portion of the DNA molecule before PCR. In still other embodiments, walking PCR is utilized. Walking PCR is a method for targeted gene walking which permits retrieval of unknown sequence (Parker et al., Nucleic Acids Res., 19:3055–60 [1991]). The PROMOTERFINDER™ kit (Clontech) uses PCR, nested primers and special libraries to "walk in" genomic DNA. This process avoids the need to screen libraries and is useful in finding intron/exon junctions.

Preferred libraries for screening for full length cDNAs include C. elegans and mammalian libraries that have been size-selected to include larger cDNAs. Also, random primed libraries are preferred, in that they will contain more sequences which contain the 5' and upstream gene regions. A randomly primed library may be particularly useful in case where an oligo d(T) library does not yield full-length cDNA. Genomic C. elegans and mammalian libraries are useful for obtaining introns and extending 5' sequence.

III. SUR-5 Polypeptides

In other embodiments, the present invention provides SUR-5 polynucleotide sequences which encode SUR-5 polypeptide sequences (see FIGS. 7, 8, 9 and 10) from the following species: C. elegans (SEQ ID NO:4, FIG. 8), human (SEQ ID NO:5, FIG. 9) and mouse (SEQ ID NO:6, FIG. 10). Other embodiments of the present invention provide fragments, fusion proteins or functional equivalents of these SUR-5 proteins. In still other embodiment of the present invention, nucleic acid sequences corresponding to these various SUR-5 homologs and mutants may be used to generate recombinant DNA molecules that direct the expression of the SUR-5 homologs and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of 20 the genetic code, DNA sequences other than the polynucleotide sequences of SEQ ID NO:1, SEQ ID NO:2, SEQ ID NO:3 which encode substantially the same or a functionally equivalent amino acid sequence, may be used to clone and express SUR-5. In general, such polynucleotide sequences hybridize to SEQ ID NOS:1, 2, and 3 under conditions of high to medium stringency as described above. As will be understood by those of skill in the art, it may be advantageous to produce SUR-5-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) can be selected, for example, to increase the rate of SUR-5 expression or to produce recombinant RNA transcripts having desirable properties, such as a longer half-life, than transcripts produced from naturally occurring sequence.

1. Vectors for Production of SUR-5

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOS:1, 2, and 3). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NOS: 1, 2, and 3) is assembled in appropriate phase with translation, initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required nontranscribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of SUR-5

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera Pseudomonas, Streptomyces, and Staphylococcus, as well as *Saccharomycees cerivisiae, Schizosaccharomycees pombe*, Drosophila S2 cells, Spodoptera Sf9 cells, Chinese hamster ovary (CHO) cells, COS-7 lines of monkey kidney fibroblasts, (Gluzman, Cell 23:175 [1981]), C127, 3T3, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, (1986)). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

3. Purification of SUR-5

The present invention also provides methods for recovering and purifying SUR-5 from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein refolding steps can be used as necessary, in completing configuration of the mature protein. In still other embodiments of the present invention, high performance liquid chromatography (HPLC) can be employed for final purification steps.

The present invention further provides polynucleotides having the coding sequence (e.g., SEQ ID NOS: 1, 2 or 3) fused in frame to a marker sequence which allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g. COS-7 cells) is used. The HA tag corresponds to an epitope derived from the influenza hemagglutinin protein (Wilson et al., Cell, 37:767 [1984]).

4. Truncation Mutants of SUR-5

In addition, the present invention provides fragments of SUR-5 (i.e., truncation mutants). In some embodiments of the present invention, when expression of a portion of the SUR-5 protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751–757 [1987]) and *Salmonella typhimurium* and its in vitro activity has been demonstrated on recombinant proteins (Miller et al., Proc. Natl. Acad. Sci. USA 84:2718–1722 [1990]). Therefore, removal of an N-terminal methionine, if desired, can be achieved either in vivo by expressing such recombinant polypeptides in a host which produces MAP (e.g., *E. coli* or CM89 or *S. cerevisiae*), or in vitro by use of purified MAP.

5. Fusion Proteins Containing SUR-5

The present invention also provides fusion proteins incorporating all or part of SUR-5. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a SUR-5 protein. In some embodiments of the present invention, the VP6 capsid protein of rotavirus is used as an immunologic carrier protein for portions of the SUR-5 polypeptide, either in the monomeric form or in the form of a viral particle. In other embodiments of the present invention, the nucleic acid sequences corresponding to the portion of SUR-5 against which antibodies are to be raised can be incorporated into a fusion gene construct which includes coding sequences for a late vaccinia virus structural protein to produce a set of recombinant viruses expressing fusion proteins comprising a portion of SUR-5 as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of SUR-5 and the poliovirus capsid protein are created to enhance immunogenicity of the set of polypeptide antigens (See e.g., EP Publication No. 025949; and Evans et al., Nature 339:385 [1989]; Huang et al., J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of SUR-5 is obtained directly from organo-chemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the SUR-5 proteins can also be expressed and presented by bacterial cells.

In addition to utilizing fusion proteins to enhance immunogenicity, it is widely appreciated that fusion proteins can also facilitate the expression of proteins, such as the SUR-5 protein of the present invention. Accordingly, in some embodiments of the present invention, SUR-5 can be generated as a glutathione-S-transferase (i.e., GST fusion protein). It is contemplated that such GST fusion proteins will enable easy purification of SUR-5, such as by the use of glutathione-derivatized matrices (See, e.g, Ausabel et al. (eds.), Current Protocols in Molecular Biology, John Wiley & Sons, New York [1991]). In another embodiment of the present invention, a fusion gene coding for a purification leader sequence, such as a poly-(His)/enterokinase cleavage site sequence at the N-terminus of the desired portion of SUR-5, can allow purification of the expressed SUR-5 fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 [1987]; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of SUR-5

Still other embodiments of the present invention provide mutant or variant forms of SUR-5 (i.e., muteins). It is possible to modify the structure of a peptide having an activity of SUR-5 for such purposes as enhancing therapeutic or prophylactic efficacy, or stability (e.g., ex vivo shelf life, and/or resistance to proteolytic degradation in vivo). Such modified peptides are considered functional equivalents of peptides having an activity of the subject SUR-5 proteins as defined herein. A modified peptide can be produced in which the amino acid sequence has been altered, such as by amino acid substitution, deletion, or addition.

Moreover, as described above, variant forms (e.g., mutants) of the subject SUR-5 proteins are also contemplated as being equivalent to those peptides and DNA molecules that are set forth in more detail. For example, it is reasonable to expect that an isolated replacement of a leucine with an isoleucine or valine, an aspartate with a glutamnate, a threonine with a serine, or a similar replacement of an amino acid with a structurally related amino acid (i.e., conservative mutations) will not have a major effect on the biological activity of the resulting molecule. Accordingly, some embodiments of the present invention provide variants of SUR-5 containing conservative replacements. Conservative replacements are those that take place within a family of amino acids that are related in their side chains. Genetically encoded amino acids are can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (See e.g., Stryer (ed.), *Biochemistry*, 2nd ed, WH Freeman and Co.[1981]). Whether a change in the amino acid sequence of a peptide results in a functional homolog can be readily determined by assessing the ability of the variant peptide to produce a response in cells in a fashion similar to the wild-type protein. Peptides in which more than one replacement has taken place can readily be tested in the same manner.

This invention further contemplates a method of generating sets of combinatorial mutants of the present SUR-5-proteins, as well as truncation mutants, and is especially useful for identifying potential variant sequences (i.e., homologs) that are functional in binding to Ras or proteins in the Ras signalling pathway. The purpose of screening such combinatorial libraries is to generate, for example, novel SUR-5 homologs which can act as either agonists or antagonists, or alternatively, possess novel activities all together.

Therefore, in some embodiments of the present invention, SUR-5 homologs are engineered by the present method to provide more efficient suppression of Ras. In other embodiments of the present invention, combinatorially-derived homologs are generated which have a selective potency relative to a naturally occurring SUR-5. Such proteins, when expressed from recombinant DNA constructs, can be used in gene therapy protocols.

Still other embodiments of the present invention provide SUR-5 homologs which have intracellular half-lives dramatically different than the corresponding wild-type protein. For example, the altered protein can be rendered either more stable or less stable to proteolytic degradation or other cellular process which result in destruction of, or otherwise inactivate SUR-5. Such homologs, and the genes which encode them, can be utilized to alter the location of SUR-5 expression by modulating the half-life of the protein. For instance, a short half-life can give rise to more transient SUR-5 biological effects and, when part of an inducible expression system, can allow tighter control of SUR-5 levels within the cell. As above, such proteins, and particularly their recombinant nucleic acid constructs, can be used in gene therapy protocols.

In still other embodiments of the present invention, SUR-5 homologs are generated by the combinatorial approach to act as antagonists, in that they are able to interfere with the ability of the corresponding wild-type protein to regulate cell proliferation.

In some embodiments of the combinatorial mutagenesis approach of the present invention, the amino acid sequences for a population of SUR-5 homologs or other related proteins are aligned, preferably to promote the highest homology possible. Such a population of variants can include, for example, SUR-5 homologs from one or more species, or SUR-5 homologs from the same species but which differ due to mutation. Amino acids which appear at each position of the aligned sequences are selected to create a degenerate set of combinatorial sequences.

In a preferred embodiment of the present invention, the combinatorial SUR-5 library is produced by way of a degenerate library of genes encoding a library of polypeptides which each include at least a portion of potential SUR-5-protein sequences. For example, a mixture of synthetic oligonucleotides can be enzymatically ligated into gene sequences such that the degenerate set of potential SUR-5 sequences are expressible as individual polypeptides, or alternatively, as a set of larger fusion proteins (e.g., for phage display) containing the set of SUR-5 sequences therein.

There are many ways by which the library of potential SUR-5 homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential SUR-5 sequences. The synthesis of degenerate oligonucleotides is well known in the art (See e.g., Narang, Tetrahedron Lett., 39:3 9 [1983]; Itakura et al., Recombinant DNA, in Walton (ed.), *Proceedings of the 3rd Cleveland Symposium on Macromolecules*, Elsevier, Amsterdam, pp 273–289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386–390 [1980]; Roberts et al., Proc. Natl. Acad. Sci. USA 89:2429–2433 [1992]; Devlin et al., Science 249: 404–406 [1990]; Cwirla et al., Proc. Natl. Acad. Sci. USA 87: 6378–6382 [1990]; as well as U.S. Pat. Nos. 5,223,409, 5,198,346, and 5,096,815, each of which is incorporated herein by reference).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of SUR-5 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Accordingly, in one embodiment of the present invention, the candidate SUR-5 gene products are displayed on the surface of a cell or viral particle, and the ability of particular cells or viral particles to bind Ras or other known Ras pathway proteins, via this gene product is detected in a "panning assay." In other embodiments of the present invention, the gene library can be cloned into the gene for a surface membrane protein of a bacterial cell, and the resulting fusion protein detected by panning (WO 88/06630;

Fuchs et al., BioTechnol., 9:1370–1371 [1991]; and Goward et al., TIBS 18:136–140 [1992]). In other embodiments of the present invention, fluorescently labeled molecules which bind SUR-5, can be used to score for potentially functional SUR-5 homologs. Cells can be visually inspected and separated under a fluorescence microscope, or, where the morphology of the cell permits, separated by a fluorescence-activated cell sorter.

In an alternate embodiment of the present invention, the gene library is expressed as a fusion protein on the surface of a viral particle. For example, foreign peptide sequences can be expressed on the surface of infectious phage in the filamentous phage system, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and fl are most often used in phage display libraries, as either of the phage gIII or gVIII coat proteins can be used to generate fusion proteins without disrupting the ultimate packaging of the viral particle (See e.g., WO 90/02909; WO 92/09690; Marks et al., J. Biol. Chem., 267:16007–16010 [1992]; Griffths et al., EMBO J., 12:725–734 [1993]; Clackson et al., Nature, 352:624–628 [1991]; and Barbas et al., Proc. Natl. Acad. Sci., 89:4457–4461 [1992]).

In another embodiment of the present invention, the recombinant phage antibody system (e.g., RPAS, Pharmacia Catalog number 27-9400-01) is modified for use in expressing and screening SUR-5 combinatorial libraries. The pCANTAB 5 phagemid of the RPAS kit contains the gene which encodes the phage gIII coat protein. In some embodiments of the present invention, the SUR-5 combinatorial gene library is cloned into the phagemid adjacent to the gIII signal sequence such that it will be expressed as a gIII fusion protein. In other embodiments of the present invention, the phagemid is used to transform competent E. coli TG1 cells after ligation. In still other embodiments of the present invention, transformed cells are subsequently infected with M13KO7 helper phage to rescue the phagemid and its candidate SUR-5 gene insert. The resulting recombinant phage contain phagemid DNA encoding a specific candidate SUR-5-protein and display one or more copies of the corresponding fusion coat protein. In some embodiments of the present invention, the phage-displayed candidate proteins which are capable of, for example, binding Ras or a protein in the Ras signalling pathway, are selected or enriched by panning. The bound phage is then isolated, and if the recombinant phage express at least one copy of the wild type gIII coat protein, they will retain their ability to infect E. coli. Thus, successive rounds of reinfection of E. coli and panning will greatly enrich for SUR-5 homologs, which can then be screened for further biological activities in order to differentiate agonists and antagonists.

In light of the present disclosure, other forms of mutagenesis generally applicable will be apparent to those skilled in the art in addition to the aforementioned rational mutagenesis based on conserved versus non-conserved residues. For example, SUR-5 homologs (both agonist and antagonist forms) can be generated and screened using, for example, alanine scanning mutagenesis and the like (Ruf et al., Biochem., 33:1565–1572 [1994]; Wang et al., J. Biol. Chem., 269:3095–3099 [1994]; Balint et al. Gene 137:109–118 [1993]; Grodberg et al., Eur. J. Biochem., 218:597–601 [1993]; Nagashima et al., J. Biol. Chem., 268:2888–2892 [1993]; Lowman et al., Biochem., 30:10832–10838 [1991]; and Cunningham et al., Science 244:1081–1085 [1989]), by linker scanning mutagenesis (Gustin et al., Virol., 193:653–660 [1993]; Brown et al., Mol. Cell. Biol., 12:2644–2652 [1992]; McKnight et al., Science 232:316); or by saturation mutagenesis (Meyers et al., Science 232:613 [1986]).

7. Chemical Synthesis of SUR-5

In an alternate embodiment of the invention, the coding sequence of sur-5 is synthesized, whole or in part, using chemical methods well known in the art (See e.g., Caruthers et al., Nucl. Acids Res. Symp. Ser., 7:215–233 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807–2817 [1981]). In other embodiments of the present invention, the protein itself is produced using chemical methods to synthesize either an entire SUR-5 amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, WH Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202–204 [1995]) and automated synthesis may be achieved, for example, using ABI 431A Peptide Synthesizer (Perkin Elmer) in accordance with the instructions provided by the manufacturer. Additionally, the amino acid sequence of SUR-5, or any part thereof, may be altered during direct synthesis and/or combined using chemical methods with other sequences to produce a variant polypeptide.

IV. Generation of Sur-5 Antibodies

Antibodies can be generated to allow for the detection of SUR-5 protein. The antibodies may be prepared using various immunogens. In one embodiment, the immunogen is a human SUR-5 peptide (e.g., an amino acid sequence as depicted in SEQ ID NO:5, or fragments thereof) to generate antibodies that recognize human SUR-5. Such antibodies include, but are not limited to polyclonal, monoclonal, chimeric, single chain, Fab fragments, and Fab expression libraries.

Various procedures known in the art may be used for the production of polyclonal antibodies directed against SUR-5. For the production of antibody, various host animals can be immunized by injection with the peptide corresponding to the SUR-5 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward SUR-5, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495–497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026–2030 [1983]) or by transforming human B cells with EBV virus in vitro (Cole et al., in *Monoclonal Antibodies and Cancer Therapy*, Alan R. Liss, pp. 77–96 [1985]).

In addition, it is contemplated that techniques described for the production of single chain antibodies (U.S. Pat. No. 4,946,778; herein incorporated by reference) will find use in producing SUR-5-specific single chain antibodies. An additional embodiment of the invention utilizes the techniques described for the construction of Fab expression libraries (Huse et al., Science 246:1275–1281 [1989]) to allow rapid and easy identification of monoclonal Fab fragments with the desired specificity for Sur-5.

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. (As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of SUR-5 (e.g., for Western blotting), measuring levels thereof in appropriate biological samples, etc. The antibodies can be used to detect SUR-5 in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of human SUR-5 using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of SUR-5 detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter Ras signal transduction. Specific antibodies that bind to the binding domains of SUR-5 or other proteins involved in Ras signalling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of Ras. Such antibodies can also be used diagnostically to measure abnormal expression of SUR-5, or the aberrant formation of protein complexes, which may be indicative of a disease state.

V. Gene Therapy Using Sur-5

The present invention also provides methods and compositions suitable for gene therapy to alter SUR-5 expression, production, or function. As described above, the present invention provides human, mouse, and *C. elegans* sur-5 genes and provides methods of obtaining sur-5 genes from other species. Thus, the methods described below are generally applicable across many species.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980–990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320–330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626–630 [1992]; See also, La Salle et al., Science 259:988–990 [1993]); and a defective adeno-associated virus vector (Samulski et al., J. Virol., 61:3096–3101 [1987]; Samulski et al., J. Virol., 63:3822–3828 [1989]; and Lebkowski et al., Mol. Cell. Biol., 8:3988–3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO94/26914). Those adenoviruses of animal origin that can be used within the scope of the present invention include adenoviruses of canine, bovine, murine (e.g., Mav1, Beard et al., Virol., 75–81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO95/02697), the E2 region (e.g., WO94/28938), the E4 region (e.g., WO94/28152, WO94/12649 and WO95/02697), or in any of the late genes L1–L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid which carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques, that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No. , 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399, 346, 4,650,764, 4,980,289 and 5,124,263; all of which are herein incorporated by reference; Mann et al., Cell 33:153 [1983]); Markowitz et al., J. Virol., 62:1120 [1988]; PCT/US95/14575; EP 453242; EP178220; Bernstein et al Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413–7417 [1987]; See also, Mackey, et al., Proc. Natl. Acad. Sci. USA 85:8027–8031 [1988]; Ulmer et al., Science 259:1745–1748 [1993]). The use of cationic lipids may promote encapsulation of negatively charged nucleic acids, and also promote fusion with negatively charged cell membranes (Felgner and Ringold, Science 337:387–388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g. Wu et al., J. Biol. Chem., 267:963–967 [1992]; Wu and Wu, J. Biol. Chem., 263:14621–14624 [1988]; and Williams et al., Proc. Natl. Acad. Sci. USA 88:2726–2730 [1991]). Receptor-mediated DNA delivery approaches can also be used (Curiel et al., Hum. Gene Ther., 3:147–154 [1992]; and Wu and Wu, J. Biol. Chem., 262:4429–4432 [1987]).

VI. Drug Screening Using Sur-5

The present invention provides methods and compositions for using SUR-5 as a target for screening drugs that can alter Ras signalling, and thus the physiological effects of Ras (e.g., effects on cell growth, differentiation, and proliferation). For example, anticancer drugs can be identified by screening for compounds that target SUR-5 or regulate sur-5 expression.

In one screening method, the two-hybrid system discussed above can be used to screen for compounds (e.g., drug) capable of altering (e.g., inhibiting) Ras/Sur-5 function(s) (e.g., signal transduction) in vitro or in vivo. In one embodiment, a GAL4 binding site, linked to a reporter gene such as lacZ, is contacted in the presence and absence of a candidate compound with a GAL4 binding domain linked to a SUR-5 fragment and a GAL4 transactivation domain II linked to a Ras fragment. Expression of the reporter gene is monitored and a decrease in the expression is an indication that the candidate compound inhibits the interaction of SUR-5 with Ras. Alternately, the effect of candidate compounds on the interaction of SUR-5 with other proteins (e.g., proteins known to interact directly or indirectly with Ras) can be tested in a similar manner.

In another screening method, candidate compounds are evaluated for their ability to alter Ras signalling by contacting SUR-5, Ras, Ras-associated proteins, or fragments thereof, with the candidate compound and determining binding of the candidate compound to the peptide. The protein or protein fragments is/are immobilized using methods known in the art such as binding a GST-SUR-5 fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 [1988]). The fusion construct is then transformed into a suitable expression system (e.g., E. coli XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate Ras-mediated physiological effects (e.g., proliferation).

In another screening method, one of the components of the Ras/SUR-5 signalling system, such as SUR-5 or a fragment of SUR-5, is immobilized. Polypeptides can be immobilized using methods known in the art, such as adsorption onto a plastic microtiter plate or specific binding of a GST-fusion protein to a polymeric bead containing glutathione. For example, GST-SUR-5 is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of SUR-5 with the other peptide. A variation of this method allows for the screening of compounds that are capable of disrupting a previously-formed protein/protein complex. For example, in some embodiments a complex comprising SUR-5 or a SUR-5 fragment bound to another peptide is immobilized as described above and contacted with a candidate compound. The dissolution of the complex by the candidate compound correlates with the ability of the compound to disrupt or inhibit the interaction between SUR-5 and the other peptide.

Another technique for drug screening provides high throughput screening for iscompounds having suitable binding affinity to SUR-5 peptides and is described in detail by Geysen (WO 84/03564). Briefly, large numbers of different small peptide test compounds are synthesized on a solid substrate, such as plastic pins or some other surface. The peptide test compounds are then reacted with SUR-5 peptides and washed. Bound SUR-5 peptides are then detected by methods well known in the art.

Another technique uses SUR-5 antibodies, generated as discussed above. Such antibodies capable of specifically binding to SUR-5 peptides compete with a test compound for binding to SUR-5. In this manner, the antibodies can be used to detect the presence of any peptide that shares one or more antigenic determinants of the SUR-5 peptide.

The present invention contemplates many other means of screening compounds. The examples provided above are presented merely to illustrate a range of techniques available. One of ordinary skill in the art will appreciate that many other screening methods can be used.

VII. Pharmaceutical Compositions Containing SUR-5 Nucleic Acid, Peptides, and Analogs The present invention further provides pharmaceutical compositions which may comprise all or portions of SUR-5 polynucleotide sequences, SUR-5 polypeptides, inhibitors or antagonists of SUR-5 bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by unwanted proliferation of cells or other Ras-mediated effects. The invention provides methods for inhibiting SUR-5 interaction with Ras and Ras-associated proteins by administering peptides or peptide fragments of SUR-5. Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, SUR-5 nucleotide and SUR-5 amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, SUR-5 polynucleotide sequences or SUR-5 amino acid sequences may be administered alone to individuals subject to or suffering from cancers characterized by Ras gain of function mutations.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of SUR-5 may be that amount that suppresses ras activation or signalling. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of SUR-5, conditions indicated on the label may include treatment of cancers resulting from ras gain of function mutations.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts SUR-5 levels.

A therapeutically effective dose refers to that amount of SUR-5 which ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for SUR-5 than for the inhibitors of SUR-5. Administration to the bone marrow may necessitate delivery in a manner different from intravenous injections.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); ng (nanograms); l or L (liters); ml (milliliters); $\mu$l (microliters); cm (centimeters); mm (millimeters); $\mu$m (micrometers); nm (nanometers); ° C. (degrees Centigrade); U (units), mU (milliunits); min. (minutes); sec. (seconds); % (percent); kb (kilobase); bp (base pair); PCR (polymerase chain reaction); BSA (bovine serum albumin); Fisher (Fisher Scientific, Pittsburgh, Pa); Sigma (Sigma Chemical Co., St. Louis, Mo.); Promega (Promega Corp., Madison, Wis.); Perkin-Elmer (Perkin-Elmer/Applied Biosystems, Foster City, Calif.); Boehringer Mannheim (Boehringer Mannheim, Corp., Indianapolis, Ind.); Clonetech (Clonetech, Palo Alto, Calif.); Quiagen (Quiagen, Santa Clarita, Calif.); Stratagene (Stratagene Inc., La Jolla, Calif.); National Biosciences (National Biosciences Inc, Plymouth Minn.)and NEB (New England Biolabs, Beverly, Mass.). Unless otherwise indicated, the restriction enzymes used in these Examples were obtained from NEB. *C. elegans* is available from the Caenorhabditis Genetics Center (CGC), at the University of Minnesota, St. Paul, Minn.

EXAMPLE 1
Isolation of Suppressor Mutants

In this Example, a screen for suppressors of the Vulvaless phenotype was conducted. Worms of the genotype unc-24 (e138)let-60(sy94)/let-65(s254) unc-22(s7) were mutagenized with 50 mM ethylmethane sulfonate (EMS) (Brenner, Genetics 77: 71–94 [1974]). The F2 progeny were screened for mutations that suppressed the Vul phenotype, (i.e., egg-laying revertants). Candidates were picked and further characterized. The Vul percentage was determined by picking L4 stage animals and counting the number of Vul animals that developed in the next two days. Two outcrosses were performed to eliminate false candidates and clean the genetic background. The first out cross was done by mating each candidate with dpy-20(e1282); him-5(e1490) males. F1 Vul animals that were picked out from the first out cross were mated to produce F2 animals. At this point, candidate intragenic suppressors were identified as dominant suppressors of Vul but not the lethal phenotype. Non-Dpy Egl+F2 animals were allowed to propagate and were used for the second out cross. The second out cross was performed by mating each surviving candidate from the first out cross to dpy-20(e1282)/dpy-20(e1362) unc-31(e169); him-5 (e1490)/+ males. Non-Dpy F1 Vul animals were picked out and mated to produce F2 animals. Non-Dpy Egl+F2 animals were picked and allowed to propagate. These animals had the genotype unc-24(e138) let-60(sy94)/dpy(e1362)unc-31 (e169); suppressor/suppressor. In these experiments, 24,000 haploid genomes were screened, and 13 independent mutations were isolated using the screen. Ten of these suppressors were extragenic suppressors, including three sur-5 alleles, while three were intragenic revertants.

EXAMPLE 2
Double Mutant Construction

In this example, sur-5 double mutants were constructed. The method for the construction of a lin-10(n1390); sur-5 (ku74) double mutant is described herein as an example of the general method used for the construction of all sur-5 (ku74) double mutants described herein. To construct the lin-10(n1390); sur-5(ku74) double mutants, lon-2(e678)sur-5(ku74); him-5(e1490) males were crossed to lin-10(n1390) hermaphrodites. F1 cross progenies were then cloned. Candidate double mutants were isolated by picking F2 progeny that were Lon and Vul. Progeny that were phenotypically Lon and Vul indicated homozygous lin-10 and possible homozygous sur-5(ku74). Each candidate's progeny were tested for the presence of the sur-5(ku74) molecular lesion, a 295 bp deletion, by polymerase chain reaction (PCR) according to well-known methods. Candidates that were Lon and Vul and contained the ku74 lesion as demonstrated by agarose gel electrophoresis were considered as lin-10 (n1390); sur-5(ku74) double mutants.

EXAMPLE 3
Characterization of Suppressor Mutants: Vul vs. Egl

In these experiments, the suppressor mutants were characterized. Six mutations were characterized with respect to the Vul and Egl phenotypes in the suppressed worms (Table 1). All of the suppressor mutations suppressed the dominant Vul phenotype of let-60(sy94dn). These mutations reduced Egl from 97% to less than 20%. Of the mutants examined, ku74 was the most effective suppressor, resulting in 99% induction of VPC's. Only 2% of these suppressed animals were Egl.

TABLE 5

Characterization of Suppressor Mutations (sur Mutations)

| Suppressor Mutations | let-60 allele[a] | % Vul[b] (n)[c] | % Vulva induction[d] (n) |
|---|---|---|---|
| + | sy94dn/+ | 97 (300) | 32 (20) |
| + | + | 0 | 100 |
| ku74 | sy94dn/+[a] | 2 (314) | 99 (25) |
| ku74 | + | 0 (100) | 100 (20) |
| ku105 | sy94dn/+ | 8 (309) | 83 (20) |
| ku105 | + | 0 (200) | 100 (21) |
| ku88 | sy94dn/+ | 17 (333) | 82 (20) |
| ku88 | + | 0 (200) | 100 (8) |
| ku87 | sy94dn/+ | 7 (321) | 98 (20) |
| ku87 | + | 0 (220) | 100 (22) |
| ku86 | sy94dn/+ | 12 (370) | 88 (20) |
| ku86 | + | 0 (180) | 100 (20) |
| ku129 | sy94dn/+ | <20 | n.d. |
| ku129 | + | 0 (100) | n.d. |

[a]The complete genotype for let-60(sy94dn)/+ is let-60(sy94dn)/dpy-20 (e1326),unc-31(e169).
[b]Percentage of hermaphrodites that are egg-laying defective.
[c]"n" indicates number of animals scored.

Dead L1 larvae were observed in the let-60 dn animals. Accordingly, the mutations that suppressed the let-60 (sy94dn) dominant Egl phenotype but did not suppress the homozygous lethal phenotype of let-60(sy94dn). In addition to the dominant Egl phenotype, heterozygous let-60(sy94dn) male worms are not able to mate due to a male tail defect caused by the let-60 dn mutation. To determine if any mutations suppressed this mating defect, males from the suppressed animals were mated to unc-24 worms. No cross progeny resulted from these crosses. Thus the suppressor mutations did not correct the mating defect of let-60 (sy94dn). Therefore, the mutations isolated according to Example 1 were specific to vulva development.

Furthermore, these mutations, when expressed in the absence of let-60(sy94dn), did not produce any detectable phenotypes. Movement and mating behaviors were identical to wild type animals. In addition, no vulva defects were observed (Table 5).

EXAMPLE 4
Characterization of Suppressor Mutants: Two Point Genetic Mapping

In these experiments, genetic mapping was conducted on mutant worms, using two point genetic mapping to assign each suppressor to one of the six chromosomes. Genetic mapping strains were constructed for each chromosome except chromosome IV. The genotypes of the mapping strains used for two-point mapping were:

dpy-20(e1282) IV; dpy-5(e61) unc-101(mI) I dpy-20(e1282) IV; dpy-10(e128) unc-4(e120) II dpy-20(e1282) IV; dpy-17(e164) unc-32(e189) III dpy-20(e1282) IV; dpy-11(e224) unc-76(e911) V dpy-20(e1282) IV; dpy-17(e164) lon-2(e678) X The mutants were mapped as follows. Isolated suppressors were mated with one of the mapping strains to test for linkage to each chromosome. In the F1 generation, Vul animals that segregated marker were picked (markers are described in Example 9). The wild-type F2 progenies were then picked individually to score for the absence of the genetic marker among the F3 animals. The absence of the genetic marker on each chromosome indicated linkage. Analysis of these experiments yielded the following results (Table 7).

TABLE 7

Two-Point Mapping Data[a]

| Suppressor | LGI Marker | LGII Marker | LGIII Marker | LGV Marker | LGX Marker |
|---|---|---|---|---|---|
| ku105 | 11/12 | 10/18 | 10/12 | 8/16 | 3/14 |
| ku74 | 2/5 | 11/17 | 5/15 | 9/17 | 3/26 |
| ku103 | 12/20 | 13/18 | 9/22 | 9/18 | 2/18 |
| ku128 | n.d. | n.d. | n.d. | n.d. | 2/9 |
| ku88 | 21/39 | 20/45 | 16/102 | 9/13 | 8/12 |
| ku86 | 46/71 | 11/17 | 19/27 | 48/79 | 13/19 |
| ku130 | n.d. | n.d. | n.d. | n.d. | 3/18 |
| ku129 | n.d. | n.d. | n.d. | n.d. | 6/24 |

[a]Shaded boxes indicate possible linkage to the indicated chromosome.

Standard complementation tests were performed for the suppressors that mapped to the X chromosome (Brenner 1974, supra). Results for these complementation tests are shown in Table 8.

TABLE 8

Complementation Data

| Genotype | Egl Percentage (n) |
|---|---|
| $\frac{\text{let-60(sy94) + }}{\text{+ dpy-20}}; \frac{\text{lon-2 ku105}}{\text{+ ku131}}(X)$ | 8(57) |

TABLE 8-continued

Complementation Data

| Genotype | Egl Percentage (n) |
|---|---|
| $\dfrac{\text{let-60(sy94)} +}{+ \text{ dpy-20}}; \dfrac{\text{lon-2 ku105}}{+ \text{ ku131}}(X)$ | 18(42) |
| $\dfrac{\text{let-60(sy94)} +}{+ \text{ dpy-20}}; \dfrac{\text{lon-2 ku105}}{+ \text{ ku74}}(X)$ | 0(22) |
| $\dfrac{\text{let-60(sy94)} +}{+ \text{ dpy-20}}; \dfrac{\text{lon-2 ku105}}{+ \text{ ku103}}(X)$ | 95(20) |
| $\dfrac{\text{let-60(sy94)} +}{+ \text{ dpy-20}}; \dfrac{+ \text{ lon-2}}{\text{ku130} +}(X)$ | 15(46) |
| $\dfrac{\text{let-60(sy94)} +}{+ \text{ dpy-20}}; \dfrac{\text{T73 lon-2}}{\text{ku129} +}(X)$ | 1(77) |

EXAMPLE 5

Characterization of Suppressor Mutants: Three Point Genetic Mapping

In these experiments, genetic mapping was conducted on mutant worms, using three point genetic mapping to assign each suppressor to a region on one of the six chromosomes. The results are presented in Table 9. The allele sur-5(ku10S) was used for all three point mapping experiments used to map sur-5. Recombinants were first isolated independently from the heterozygous animals. Each homozygous recombinant was tested for the presence of sur-5(ku105) using complementation tests. These were performed by crossing the recombinant animals to let-60(sy94dn)/dpy-20(e1282) let-60(sy130gf); lon-2(e678)sur-5(ku105) males. The F1 cross progenies were picked individually and scored for the presence of the Vul phenotype. The genotype of each F1 cross progeny was determined by observing the segregation of genetic markers in their F2 progenies.

TABLE 9

Genetic Three Point Mapping Data

| Heterozygote Genotype | Recombinant Phenotype | Recombinant with Suppressor/Total Recombinants |
|---|---|---|
| $\dfrac{\text{let-60dn} +}{+ \text{ unc-22}}; \dfrac{+ \text{ sur-5} +}{\text{lon-2} + \text{dpy-6}}(X)$ | Lon non-Dpy* | 6/13 |
| $\dfrac{\text{lon-2} + \text{sur-5} +}{\text{lon-2 unc-6} + \text{dpy-7}}(X)$ | Unc non-Dpy | 6/10 |
| $\dfrac{\text{lon-2} + \text{sur-5} +}{\text{lon-2 unc-6} + \text{dpy-7}}(X)$ | Dpy non-Unc | 3/7 |
| $\dfrac{\text{lon-2 sur-5} + +}{+ + \text{unc-18 dpy-6}}(X)$ | Unc non-Dpy | 0/5 |

TABLE 9-continued

Genetic Three Point Mapping Data

| Heterozygote Genotype | Recombinant Phenotype | Recombinant with Suppressor/Total Recombinants |
|---|---|---|
| $\dfrac{\text{lon-2 sur-5} + +}{+ + \text{unc-18 dpy-6}}(X)$ | Dpy non-Unc | 5/5 |
| $\dfrac{\text{let-60dn} +}{+ \text{ unc-22}}; \dfrac{+ + \text{ku88}}{\text{dpy-18 unc-25}}(III)$ | Unc non-Dpy* | 0/6 |
| $\dfrac{\text{let-60dn} +}{+ \text{ unc-22}}; \dfrac{+ \text{ku87} +}{\text{bli-2 rol-1}}(II)$ | Rol non-Bli* | 3/15 |
| $\dfrac{\text{let-60dn} +}{+ \text{ unc-22}}; \dfrac{\text{ku129} + +}{+ \text{ lon-2 dpy-6}}(X)$ | Lon non-Dpy* | 0/9 |
| $\dfrac{\text{let-60(sy94)} +}{+ \text{ dpy-20}}; \dfrac{+ \text{ku86} +}{\text{unc-60 dpy-11}}(V)$ | Unc non-Dpy* | 9/17 |

Using these techniques, sur-5 mapped to a small region between two cloned genes, unc-6 and dpy-7, on chromosome X. unc-6 and dpy-7 served as molecular markers that defined the left and right end positions for sur-5 on the physical map. The genetic position of the suppressors is shown below:

TABLE 10

Map Position of Suppressors

| Suppressor | Linkage Group | Map Position |
|---|---|---|
| ku74 | X | maps between unc-6 and dpy-7, an allele of sur-5 |
| ku131 | X | an allele of sur-5 |
| ku105 | X | an allele of sur-5 |
| ku88 | III | right of unc-25 |
| ku87 | II | between bli-2 and rol-1 |
| ku86 | V | between dpy-11 and unc-60 |
| ku130 | X | left of lon-2 |
| ku129 | X | failed to complement ku130 |
| ku89 | IV | possible intragenic revertant |
| ku85 | IV | possible intragenic revertant |
| ku72 | IV | possible intragenic revertant |
| ku128 | — | ku1218 is not on X |

The sur-5 gene was defined by four allelic suppressor mutations on chromosome X: ku74, ku105, ku103 and ku131 which failed to complement ku74. The complementation data are listed below in Table 11. These four suppressors mapped between unc-6 and dpy-7 of the X chromosome. ku87 mapped between bli-2 and rol-1 on chromosome II, and ku88 mapped to the right of or close to unc-25 on chromosome III. ku86 mapped between dpy-11 and unc-60 on chromosome V. ku130 and ku129 were allelic and mapped to the left of or close to lon-2 on chromosome X. The position of ku128 was not determined. All sur-5 mutant alleles were similar. All reverted the let-60(sy94dn) dominant Vul phenotype to wild type, and all failed to suppress the homozygous lethal phenotype as well as the male mating defect of let-60(sy94dn).

TABLE 11

Complementation of sur-5 alleles.

| Genotype | % Vul (n) |
|---|---|
| let-60(sy94dn)/dpy-20(e1362)unc-31(e196);sur-5(ku105)lon-2(e678)/sur-5(ku105) lon-2(e678) | 8 (309) |
| let-60(syn94dn)/dpy-20(e1282);sur-5 (ku105)lon-2(e678)/sur-5(ku103) | 0 (22) |
| let-60(sy94dn)/dpy-20(e1282);sur-5(ku105)lon-2(e678)/sur-5 (ku74) | 18 (42) |
| let-60(sy94dn)/dpy-20(e1282);sur-5(ku105)lon-2(e678)/sur-5(ku131) | 8 (57) |

EXAMPLE 6

Genetic Interactions Between sur-5 and Known Mutations

To further characterize the action of sur-5 in the let-60 ras pathway, double mutants between sur-5(ku74) and other loss-of-function mutations in the let-60 pathway were created as desribed in Example 2. There are two classes of mutations in the syn-Muv pathway: class A and class B. The class A and B genes probably define two functionally redundant pathways that negatively regulate vulval induction. Since sur-5 negatively regulated let-60, and sur-5 mutations do not have any phenotypes of their own, the sur-5 may have been a syn-Muv gene. To test this, double mutants between sur-5(ku74) and either the class A mutation lin-8(n111) or the class B mutation lin-9(n112) were created. Mutations in either class have no independent phenotypes. However, double mutations between classes A and B show the Muv phenotype. The lin-15 n765 allele is mutated in both class A and class B genes and it is temperature sensitive. At 20° C. the VPC 's were induced to 200%. At 17° C., the VPC's were induced to less than 200%. Accordingly, all sur-5; lin-15 experiments were performed at 17° C. The vulva phenotypes of tlese double mutants were then examined to determine if there were any epistatic relationships (Table 12).

TABLE 12

Genetic Interactions Between sur-5(ku74) and Other Mutations

| sur-5 allele | Other Mutation | % Egl (n) | % VPC Induction (n) |
|---|---|---|---|
| + | let23(sy1);lon-2(e678) | 71 (187) | 15 (12) |
| ku74 | let23(sy1);lon-2(e678)sur-5(ku74) | 75 (175) | 13 (10) |
| + | lon-2(e678)sem-5(n2019) | 92 (234) | nd |
| ku74 | lon-2(e678)sur-5(ku74)sem-5(n2019) | 91 (295) | nd |
| + | let-60 (n2021);lon-2(e678) | 21 (141) | 88 (20) |
| ku74 | let-60(n2021);lon-2(e678)sur-5(ku74) | 27 (124) | 90 (19) |
| + | unc-24(e138)lin-45(sy96);lon-2(e678) | 96 (124) | 30 (12) |
| ku74 | uc-24(e138)lin-45(sy96);lon-2(e678)sur-5(ku74) | 97 (140) | 28 (10) |
| + | dpy-17(e164)sur-1(ku1) | nd[a] | 85 (15) |
| ku74 | dpy-17(e164)sur-1(ku1);lon-2(e678),sur-5(ku74) | nd | 81 (11) |
| + | lin-15(n765);lon-2(e678) | nd[a] | 110 (12[b]) |
| ku74 | lin-15(n765);lon-2(e678),sur-5(ku74) | nd | 119 (17) |
| + | lin-10(e1439);lon-2(e678) | 84 (124) | nd |
| ku74 | lin-10(e1439);lon-2(e678),sur-5(ku74) | 88 (212) | nd |
| + | dpy-10(e128),lin-8(n111) | 0 (180) | 100 (20) |
| ku74 | dpy-10(e128),lin-8(n111);lon-2(e678),sur-5(ku74) | 0 (200) | 100 (20) |

TABLE 12-continued

Genetic Interactions Between sur-5(ku74) and Other Mutations

| sur-5 allele | Other Mutation | % Egl (n) | % VPC Induction (n) |
|---|---|---|---|
| + | dpy-17(e164),lin-9(n112) | 0 (200) | 100 (22) |
| ku74 | dpy-17(e164),lin-9(n112);lon-2(e678),sur-5(ku74) | 0 (200) | 99.6 (48) |

[a]The percent Egl animals were not recorded because Egl and exploding gonad phenotypes were not distinguishable.
[b]all sur-5;lin-15 experiments were conducted at 17° C.

No mutant vulval phenotypes were detected from the double mutant between sur-5(ku74) and either the class A Muv mutation lin-8(n111) or the class B mutation lin-9 (n112)(Table 12). Accordingly, sur-5 is not one of the syn-Muv genes.

To determine if sur-5 functioned in parallel to the syn-Muv pathway further double mutants were created using the methods of Example 2. A double mutant was created between sur-5(ku74) and lin-15(n765) to determine whether or not sur-5 enhanced the Muv phenotype of the lin-15 mutation. The lin-15 locus negatively regulates the let-60 pathway, and belongs to the syn-Muv family of genes. The n765 allele is temperature sensitive, and at 20° C. the VPC's were 200% induced. Double mutant experiments were performed at 17° C. as the VPC's were induced to less than 200%. As can be seen in Table 12, sur-5(ku74) did not enhance the Muv phenotype of lin-15(n765).

EXAMPLE 7

Genetic Interactions Between sur-5 and let-60 dn Mutations

To determine if sur-5(ku74) suppression of the dominant Vul phenotype of let-60(sy94dn) was allele specific, sur-5 suppression of other let-60 dn mutations was examined (Table 13).

TABLE 13

Genetic Interactions Between sur-5(ku74) and let-60 dn Alleles

| sur-5 Genotype | let-60 dn Genotype | % Egl (n) | % VPC Differentiation (n) |
|---|---|---|---|
| + | N2 | 0 | 100 |
| ku74 | dpy-20(e1282)lon-2(e678)sur-5(ku74) | 0 (200) | 100 (20) |
| + | let-60(sy94)/dpy-20(e1282);lon-2(e678)/+ | 97 (300) | 33 (12) |
| ku74 | let-60(sy94)/dpy-20(e)unc-31;lon-2(e678)sur-5(ku74)/+ | 2 (314) | 99 (25) |
| + | let-60(sy101)dpy-20(e1282)/unc-22(s9);lon-2(e678)/+ | 80 (170) | 35 (18) |
| ku74 | let-60(sy101)dpy-20(e1282)/unc22(s9);lon-2(e678)sur-5(ku74)/+ | 9 (247) | 90 (20) |
| + | let-60(n1531)/dpy-20(e1282);lon-2(e678)/+ | 88 (228) | 44 (17) |
| ku74 | let-60(n1531)/dpy-20(e1282);lon2(e678)sur-5(ku74)/+ | 4 (418) | 89 (14) |
| + | let-60(n2031)/dpy-20(e1282);lon-2(e678)/+ | 33 (220) | 81 (16) |
| ku74 | let-60(n2031)/dpy-20(e1282);lon-2(e678)sur-5(ku74)/+ | 1 (310) | 99 (21) |
| + | let-60(sy93)/dpy-20(e1282);lon-2(e678)/+ | 95 (200) | 5 (12) |
| ku74 | let-60(sy93)/dpy-20(e1282);lon-2(e78)sur-5(ku74)/+ | 95 (180) | 6 (10) |

TABLE 13-continued

Genetic Interactions Between sur-5(ku74) and let-60 dn Alleles

| sur-5 Genotype | let-60 dn Genotype | % Egl (n) | % VPC Differentiation (n) |
|---|---|---|---|
| + | let-60(sy100),dpy-20(e1282)/unc-22(s9);lon-2(e678)/+ | 25 (418) | 70 (22) |
| ku74 | let-60(sy100),dpy-20(e1282)/unc-22(s9);lon-2(e678)sur-5 (ku74)/+ | 25 (257) | 65 (14) |

From these experiments, it was determined that sur5 (ku74) suppressed four let-60dn alleles, sy94, sy101, n1531, and n2301 but fails to suppress two other let-60dn alleles, sy93 and sy100.

EXAMPLE 8
Deficiency Studies

This example describes experiments to determine the phenotype of the sur-5(ku74)/deficiency. The genetic distance between unc-6 and dpy-7 is only 0.37 map units on the X chromosome; sur-5 mapped between 0.14 and 0.16 map units to the left of dpy-7. This region falls under the deficiency uDf1 on the genetic map. The deficiency uDf1 uncovers unc-6 and dpy-7, and because sur-5 maps in this region, uDf1 uncovers sur-5.

A lon-2(e678) sur-5(ku74)/uDf1 strain was constructed. lon-2(e678) sur5(ku74); him-5(e1490) males were crossed with a single +/szT1[lon-2(e678)]I; uDf1/szT1X hermaphrodite. Each non-Lon F1 progeny was picked individually, examined on a plate and its phenotype recorded. UDf1/+ and uDf1/lon-2(e678) sur-5(ku74) animals have a 10% Egl phenotype. This phenotype is independent of VPC induction, indicating sur5(Ku74)/uDf1 is wild-type for VPC induction. The genotype of each F1 progeny was determined by examination of genetic markers in the F2 generation.

To determine the suppression of the let-60(sy94dn) Vul phenotype by sur-5(ku74)/uDf1, animals with the genotype let-60(sy94dn)/+; lon-2(e678) sur-5(ku74)/uDf1 were constructed. let-60(sy94dn)/let-60(sy130gf)dpy-20(e1282); lon-2(e678) sur-5(ku74); him-5(e1490) males were crossed with a single +/szT1[lon-2(e678)I; uDf1/szT1X hermaphrodite. Non-Lon F1 progeny were picked onto microscope slides and scored for VPC induction percentage using a compound microscope. Each animal was then recovered from the slide and placed onto individual plates where the animal produced the F2 progeny. The F1 genotype was determined by examining the genotype of the F2 progeny. Only data from F1 cross progeny with the desired genotype were used in the experimental analysis (Table 14).

TABLE 14

Deficiency Study of sur-5(ku74)

| Genotype | % VPC Induction (n) |
|---|---|
| let-60(sy94dn)/+;lon-(e678)sur5(ku74)/uDF-1 | 88 (10) |
| let-60(sy94dn)/dpy-20(e)unc-36;sur5(ku74)/sur-5(ku74) | 99 (25) |

From these data, it was not evident whether uDf1/sur-5 (ku74) suppressed the dominant Vul phenotype of let-60 (sy94dn) better or equal to the homozygous sur-5(ku74). Therefore, it was not clear whether sur-5(ku74) was a partial loss-of-function mutation or a null mutation.

EXAMPLE 9
Cosmid Analysis and Microinjection Transformation

In these experiments, the sur-5 gene was further analyzed using cosmid analysis. The region of the physical map that corresponded to the position of sur-5 was covered by overlapping cosmids obtained from A. Coulson and J. Sulston (Sanger Center, MRC Laboratory of Molecular Biology, Cambridge, UK). DNA isolation, analysis and sub-cloning were performed by standard molecular biology methods.

Cosmids were tested for the presence of the sur-5 gene by DNA-mediated gerrnline microinjection transformation using coinjections of 100 ng/µl of the pRF4 plasmid as the transformation marker. pRF4 contains dominant rol-6 mutant DNA which can serve to identify transformed cells. Microinjection of cloned DNA's into the gonadal syncytia of C. elegans hermaphrodites was carried as previously described (Mello et al., EMBO J., 10: 3959–3970 [1991]).

Cosmids ZK867, R06C11, C56G3, K08E2, C34H12, C07D8, F46H5, T08A9, K03A1, R12E12 were initially injected as a pool of four overlapping cosmids at a concentration of approximately 12 ng/µl each. A let-60(sy94dn)/dpy-20(e1362) unc-31(e169); Ion-2(e678)sur-5(ku105) strain (Vul<15%) was used as the host strain for microinjection. DNA rescue was assayed by scoring injection-transformed host animals for reversion of the suppressor phenotype of sur-5(ku74) on the let-60 dominant Vul phenotype. Rescue of the sur-5 mutant phenotype was indicated by >40% Vul phenotype. Each injection was scored with at least four independent transgenic lines. The extent of rescue was not consistent between the different lines. Positive cosmids were then injected individually at a concentration of about 60 ng/µl. Two overlapping cosmids, K03A1 and R12E12 were identified that were each capable of rescuing the sur-5(ku74) suppression phenotype.

The overlapping region of the two cosmids was further characterized by sub-cloning and microinjection. Subclones were first injected as a pool of four non-overlapping subdlones at a concentration of ~15 ng/µl each. Subdlones from positive pools were then injected individually at a concentration of ~15 ng/µl each. An 8 kb Bam HI restriction fragment (subclone pTG1, described below) rescued the sur-5 mutant phenotype. In addition, this plasmid also rescued a strain that was let-60(sy94dn)/dpy-20(e1362)unc-31 (e169); sur-5(ku74).

The plasmid pTG11 contained an additional 1.8 kb long segment 5' upstream of the sur-5 5' flanking sequence of pTG1. PTG11 also rescued let-60(sy94dn)/dpy-20(e1362) unc-31(e169); sur-5(ku74). When pTG11 was injected at concentrations of ~45 ng/µl and ~60 ng/µl into wild-type animals, no mutant phenotypes were observed. These microinjections were also performed using pRF4 injected at ~100 ng/µl as the transformation marker.

EXAMPLE 10
Northern Blots and cDNA Isolations

In this experiment, expression of sur-5 was analyzed by Northern blotting. pTG1 was used as a template for producing radioactive probes for Northern blot analysis. Northern blot analysis was performed with staged C. elegans total RNA fractions and mRNA using standard techniques. Low levels of a single 2.2 kb band were detected in L1, L2, and L4 stage total RNA's and in poly(A)+ early embryonic mRNA.

pTG1 was also used to screen approximately one million plaques from a lambda gt11 early embryonic cDNA library (a gift from P. Okkemma and A. Fire). Four positive clones were identified. All four cDNA clones had the same sur-5 gene sequence. In addition, all four cDNA clones lacked one or two nucleotides that would have completed the cDNA sequence, and therefore, the first amino acid codon for methionine was incomplete.

EXAMPLE 11
DNA Sequencing and Determination of sur-5 Molecular Lesions cDNA and genomic DNA from wild-type *C. elegans* were sequenced using a double stranded DNA sequencing method utilizing a Sequenase kit (USB). Both genomic and cDNA sequences were obtained by directly sequencing the PCR products after purification from agarose gels. The DNA sequence is shown in FIG. 4.

To determine the molecular lesions of the sur-5 mutant alleles that were identified, all sur-5 exons and exon/intron boundaries were sequenced as above. These sequences were generated from gel purified DNA that had been PCR-amplified from wild-type animals and sur-5 mutants. The sur-5(ku74) mutant cDNA contained a 295 base pair in-frame deletion. The 295 base pair deletion results in the deletion of 70 amino acids (amino acid 76–145) and also results in the creation of an extra threonine amino acid.

EXAMPLE 12
Sequence Homology Determination

The wild-type sur-5 cDNA sequence (SEQ ID NO:1) determined above predicted a protein of 700 amino acids (SEQ ID NO:4, FIGS. 7 and 8).

The computer program PROSITE (distributed by EMBO Laboratory) predicts that sur-5 potentially has one ATP/GTP binding and two AMP binding motifs. Amino acids 3–10, AVSANGKT (SEQ ID NO:11), fit a consensus sequence [AG]-X(4)-G-K-[ST] (SEQ ID NO:16) for an ATP/GTP binding motif (P-loop [AG] means either A or G; X(4) means any 4 amino acids in a row). Amino acids 315–327, VMFSSGTTGIPK (SEQ ID NO:12), are predicted as the AMP binding motif with the consensus sequence of [LIVMFY]-X(2)-[STG]-[STAG]-G-[ST]-[STEI]-[SG]-X-[PASLIUM]-[KR] (SEQ ID NO:13). Another possible AMP binding motif is identified at the C-terminus of the sur-5 amino acid sequence. The C-terminal half of the protein has a relatively weak sequence homology (~22% amino acid identity) to the acetyl-CoA synthetase protein family and Histone acetyl-transferases (HAT). At the C-terminus of acetyl-CoA synthetase, there is an AMP binding consensus. Amino acids 658–669 of sur-5, PYTSSGKKVEV (SEQ ID NO:14), are similar to the consensus P-K-T-[RVL]-S-G-K-[IVT]-[TMVK]-R-[RN] (SEQ ID NO:15). While it is not intended that the present invention be limited to any one particular hypothesis, these sequence similarities suggest that the SUR-5 protein performs a biochemical function that requires ATP/AMP binding. The similarity to acetyl-CoA synthetases may suggest a function that involves the molecule acetyl-CoA.

In order to search for homologs of *C. elegans* sur-5, the predicted sur-5 amino acid sequence was used to search for homologous sequences from other organisms. Using the computer program BLAST (Basic Local Alignment Search Tool, National Center for Biotechnology Information, National Library of Medicine, National Institutes of Health, United States), mouse and human sur-5 homologs (about 200 bp) in the EST database, were identified. Approximately $3 \times 10^6$ plaques in mouse thymus and human brain cDNA libraries (Stratagene) were screened using lambda reverse or forward primers as the 5' end primer and specific EST sequences as the downstream 3' primer. Both PCR screening of mouse thymus and human brain cDNA libraries and the 5' Erase method on human RNA were used to clone the full length or major part of the human sur-5 cDNA.

The C-terminus residues (361 to 700) of *C. elegans* sur-5 were significantly homologous with the available mouse and human homologs. Using the program BESTFIT for analysis of degree of homology between the amino acid sequences, 35% homology between the *C. elegans* sur-5 and either the mouse or human sur-5 homologs was calculated. Furthermore, there was 90% homology between the mouse sur-5 homolog and the human sur-5 homolog. Because of the high level of amino acid identity, sur-5 appears to be conserved during evolution (FIG. 7).

EXAMPLE 13
Expression of sur-5 In Vivo -Fusion Proteins

To visualize the expression of sur-5 in vivo, several fusions of SUR-5 with green fluorescent protein (GFP) vectors (gift from A. Fire) were created as follows. Genomic sur-5 DNA was fused just before the stop codon in frame to the sequence of the various GFP vectors. A 339 base pair DNA fragment was first amplified by PCR using the following primers:

5' AACTGCAGGAGGGCATGGACGAGGAA 3' (SEQ ID NO:7) and

5' TCCCCCCGGGAAGTCTGTATTGAACGAAAT 3' (SEQ ID NO:8)

from pTG1. This fragment included the last 327 nucleotides just before the stop codon. This fragment was cloned into PstI/SmaI sites of pBluescript (Stratagene). After sequencing the fragment, the 231 bp BspEI/SmaI fragment was cut out and used to replace the SmaI/BspEI fragment of pTG1_1 to create the plasmid pTG1_3. The SphI/SmaI fragment of pTG1_3 was then cloned into the SphI/SmaI sites of the GFP-containing vector pPD95.70 to create the plasmid pTG96, and the SphI/SmaI sites of pPD95.79 to create the plasmid pTG96_1. To create the SUR-5/GFP transcriptional fusion protein, the 3.68 kb 5' flanking DNA upstream of sur-5 from pTG1_1 was amplified using PCR. The primers used were:

5' GCCAAGCTTGCATGCCTGCA 3'(SEQ ID NO:9) and

5' GCTCTAGACATTCTGAAAACAAAATCTAAA 3' (SEQ ID NO:10).

The 3' end of this PCR fragment included the first amino acid methionine of sur-5 in frame with linker amino acids whose DNA sequence comprised an XbaI site. In addition, the 3.68 kb fragment presumably included the entire 5' promoter sequence in addition to the full length sur-5 genomic and an artificial nuclei localization sequence (NLS). This PCR product was cut by XbaI and SphI and then cloned into SphI/XbaI sites of pPD95.69 to create pTG96_2.

All constructs were individually microinjected into worms, and the progeny that showed green fluorescence were examined in detail. Those progeny that were fluorescent were deemed to express reasonable levels of the fusion proteins, and were further examined.

When the SUR-5/GFP fusion proteins from pTG96 were expressed from an extrachromosomal array, kuEx75, the SUR-5/GFP fiision proteins were tightly localized to the nuclei of most cells, including strong expression in vulva cells. Neurons, hypodermis, Pn.p cells, body muscles, many cells of the pharynx and a few cells of the somatic gonad all fluoresced. The cells that did not fluoresce include B,F, K', K.a, K.p, hyp3, the germline and the excretory duct cell. In non-mosaic animals, the intensity often varied between cell types. For example, the intestine cells and excretory cells were almost always very bright, whereas neurons were almost always fainter. Uterine cells and many of the cells derived from the M cell were very faint and often difficult to see.

The SUR-5/GFP fusion proteins were expressed in all stages of *C. elegans* development. The earliest expression observed was at 100–150 cells of the embryonic stage. The same expression pattern was seen after this array was integrated into one of the chromosomes.

When the SUR-5/GFP construct pTG96_1 was expressed, the fusion proteins were also localized to the nuclei, even though pTG96_1 did not contain the NLS that was contained in pTG96. The expression pattern was found to be the same as the expression pattern seen for the kuEx75 array, but the nuclear localization was not as tight. There was some diffusion of the SUR-5/GFP proteins from the nucleus to the cytoplasm. The extrachromosomal array kuEx75 was able to efficiently rescue the sur-5 suppression of the let-60 (sy94dn) phenotype. Accordingly, sur-5 retained the wild type function. It was found that sur-5 is expressed in the nucleus and can play a role in the cytoplasm.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, or related fields are intended to be within the scope of the following claims.

What is claimed is:

1. An isolated nucleic acid comprising a polynucleotide sequence selected from the group consisting of SEQ ID NO 1 and SEQ ID NO 2.

2. A vector comprising the nucleic acid of claim 1.

3. An isolated host cell comprising the vector of claim 2.

4. The host cell of claim 3, wherein said host cell is selected from the group consisting of bacterial, yeast, insect, amphibian and mammalian cells.

5. A nucleic acid sequence encoding an amino acid sequence selected from the group consisting of SEQ ID NO 4 and SEQ ID NO 5.

6. A vector comprising the nucleic acid of claim 5.

7. An isolated host cell comprising the vector of claim 6.

8. The host cell of claim 7, wherein said host cell is selected from the group consisting of bacterial, yeast, insect, amphibian and mammalian cells.

9. An isolated nucleic acid consisting of the nucleotide sequence of SEQ ID NO 3.

10. A vector comprising an insert consisting of the nucleic acid of claim 9.

11. An isolated nucleic acid comprising a polynucleotide sequence selected from the group consisting of SEQ ID NO 7 and SEQ ID NO 8.

12. A method of detecting a nucleic acid encoding a candidate SUR-5 protein, comprising:
   i. providing:
      (a) a biological sample suspected of containing a nucleic acid sequence encoding a SUR-5 protein, and
      (b) a polynucleotide probe comprising a polynucleotide sequence selected from the group consisting of SEQ ID NO 1 and SEQ ID NO 2;
   ii. hybridizing said polynucleotide probe to said nucleic acid sequence suspected of encoding a SUR-5 protein to produce a hybridization complex; and detecting the presence of said hybridization complex, wherein the presence of a positive hybridization signal indicates that said nucleic acid encodes a candidate SUR-5 protein.

* * * * *